United States Patent
Komuro et al.

(10) Patent No.: US 9,218,053 B2
(45) Date of Patent: Dec. 22, 2015

(54) SURGICAL ASSISTANT SYSTEM

(71) Applicant: OLYMPUS CORPORATION, Tokyo (JP)

(72) Inventors: Takahiro Komuro, Tokyo (JP); Masatoshi Iida, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/168,551

(22) Filed: Jan. 30, 2014

(65) Prior Publication Data
US 2014/0148818 A1 May 29, 2014

Related U.S. Application Data

(63) Continuation of application No. PCT/JP2012/070581, filed on Aug. 6, 2012.
(60) Provisional application No. 61/515,203, filed on Aug. 4, 2011.

(30) Foreign Application Priority Data

Feb. 29, 2012 (JP) .................................. 2012-043487

(51) Int. Cl.
*A61B 1/00* (2006.01)
*A61B 1/04* (2006.01)
(Continued)

(52) U.S. Cl.
CPC . *G06F 3/01* (2013.01); *A61B 17/29* (2013.01); *A61B 17/32002* (2013.01);
(Continued)

(58) Field of Classification Search
CPC ........... A61B 19/2203; A61B 19/5244; A61B 19/5212; A61B 2019/2223; A61B 19/56; A61B 1/0005; A61B 19/5225; A61B 1/00149; A61B 5/742; G06T 2207/10068
USPC ........................................................ 600/102
See application file for complete search history.

(56) References Cited

U.S. PATENT DOCUMENTS 4,830,569 A 5/1989 Jannborg
5,214,969 A 6/1993 Adkins et al.
(Continued)

FOREIGN PATENT DOCUMENTS

CN 101426412 A 5/2009
DE 10 2008 041 867 A1 3/2010
(Continued)

OTHER PUBLICATIONS

English Abstract of JP 01-234140 dated Sep. 19, 1989.
(Continued)

*Primary Examiner* — John P Leubecker
*Assistant Examiner* — Ronald D Colque
(74) *Attorney, Agent, or Firm* — Scully, Scott, Murphy & Presser, PC

(57) ABSTRACT

A surgical assistant system includes: an operation unit configured to give an input; an arm unit on which a treatment tool is mounted; an operation imaging unit configured to acquire an operation image that is an image including the operation unit; an endoscope configured to acquire an internal-body image; a mode control unit having a plurality of operation modes and configured to enable one of the plurality of operation modes to be set as a setting operation mode; a driving unit configured to enable the arm unit to be operated based on the input given by the operation unit and the setting operation mode; a synthetic image creation unit configured to synthesize images using at least the operation image to create a synthetic image based on the setting operation mode; and a display unit configured to display the synthetic image.

11 Claims, 9 Drawing Sheets

(51) Int. Cl.
*G06F 3/01* (2006.01)
*A61B 19/00* (2006.01)
*A61B 17/29* (2006.01)
*A61B 17/32* (2006.01)
*A61B 18/14* (2006.01)
*A61B 19/08* (2006.01)
*B25J 13/02* (2006.01)
*A61B 17/068* (2006.01)
*A61B 19/10* (2006.01)
*A61B 17/00* (2006.01)

(52) U.S. Cl.
CPC .......... *A61B 18/1402* (2013.01); *A61B 19/081* (2013.01); *A61B 19/22* (2013.01); *A61B 19/2203* (2013.01); *A61B 19/26* (2013.01); *A61B 19/44* (2013.01); *B25J 13/02* (2013.01); *A61B 17/068* (2013.01); *A61B 19/10* (2013.01); *A61B 19/5244* (2013.01); *A61B 19/56* (2013.01); *A61B 2017/00119* (2013.01); *A61B 2017/00477* (2013.01); *A61B 2017/00482* (2013.01); *A61B 2019/2223* (2013.01); *A61B 2019/2269* (2013.01); *A61B 2019/2292* (2013.01); *A61B 2019/2296* (2013.01); *A61B 2019/465* (2013.01); *A61B 2019/467* (2013.01); *A61B 2019/4815* (2013.01); *A61B 2019/4868* (2013.01); *A61B 2019/4873* (2013.01); *A61B 2019/5255* (2013.01); *A61B 2019/5289* (2013.01); *Y10S 901/08* (2013.01); *Y10S 901/09* (2013.01); *Y10S 901/30* (2013.01); *Y10T 29/49826* (2015.01); *Y10T 74/18056* (2015.01)

(56) References Cited

U.S. PATENT DOCUMENTS

| | | | |
|---|---|---|---|
| 5,603,723 A | 2/1997 | Aranyi et al. | |
| 5,632,432 A | 5/1997 | Schulze et al. | |
| 5,649,956 A | 7/1997 | Jensen et al. | |
| 5,656,903 A | 8/1997 | Shui et al. | |
| 5,712,543 A | 1/1998 | Sjostrom | |
| 5,762,458 A | 6/1998 | Wang et al. | |
| 5,836,869 A * | 11/1998 | Kudo et al. | 600/173 |
| 5,855,583 A | 1/1999 | Wang et al. | |
| 5,871,493 A | 2/1999 | Sjostrom et al. | |
| 6,007,550 A | 12/1999 | Wang et al. | |
| 6,063,095 A | 5/2000 | Wang et al. | |
| 6,090,122 A | 7/2000 | Sjostrom et al. | |
| 6,102,850 A | 8/2000 | Wang et al. | |
| 6,132,368 A | 10/2000 | Cooper | |
| 6,132,441 A | 10/2000 | Grace | |
| 6,206,903 B1 | 3/2001 | Ramans | |
| 6,246,200 B1 | 6/2001 | Blumenkranz et al. | |
| 6,328,752 B1 | 12/2001 | Sjostrom et al. | |
| 6,346,072 B1 | 2/2002 | Cooper | |
| 6,430,473 B1 | 8/2002 | Lee et al. | |
| 6,436,107 B1 | 8/2002 | Wang et al. | |
| 6,441,577 B2 | 8/2002 | Blumenkranz et al. | |
| 6,557,558 B1 * | 5/2003 | Tajima et al. | 128/897 |
| 6,574,355 B2 | 6/2003 | Green | |
| 6,587,750 B2 | 7/2003 | Gerbi et al. | |
| 6,602,185 B1 * | 8/2003 | Uchikubo | 600/118 |
| 6,645,196 B1 | 11/2003 | Nixon et al. | |
| 6,666,876 B2 | 12/2003 | Kawai et al. | |
| 6,676,684 B1 | 1/2004 | Morley et al. | |
| 6,685,698 B2 | 2/2004 | Morley et al. | |
| 6,699,177 B1 | 3/2004 | Wang et al. | |
| 6,746,443 B1 | 6/2004 | Morley et al. | |
| 6,783,524 B2 | 8/2004 | Anderson et al. | |
| 6,786,896 B1 | 9/2004 | Madhani et al. | |
| 6,853,879 B2 | 2/2005 | Sunaoshi | |
| 6,866,671 B2 | 3/2005 | Tierney et al. | |
| 6,905,460 B2 | 6/2005 | Wang et al. | |
| 6,913,613 B2 | 7/2005 | Schwarz et al. | |
| 7,083,571 B2 | 8/2006 | Wang et al. | |
| 7,101,363 B2 | 9/2006 | Nishizawa et al. | |
| 7,107,124 B2 * | 9/2006 | Green | 700/245 |
| 7,118,582 B1 | 10/2006 | Wang et al. | |
| 7,273,488 B2 | 9/2007 | Nakamura et al. | |
| 7,295,893 B2 | 11/2007 | Sunaoshi | |
| 7,313,464 B1 | 12/2007 | Perreault et al. | |
| 7,331,967 B2 | 2/2008 | Lee et al. | |
| 7,357,774 B2 | 4/2008 | Cooper | |
| 7,422,592 B2 | 9/2008 | Morley et al. | |
| 7,476,237 B2 | 1/2009 | Taniguchi et al. | |
| 7,549,998 B2 | 6/2009 | Braun | |
| 7,608,083 B2 | 10/2009 | Lee et al. | |
| 7,654,431 B2 | 2/2010 | Hueil et al. | |
| 7,666,191 B2 | 2/2010 | Orban, III et al. | |
| 7,674,255 B2 | 3/2010 | Braun | |
| 7,695,481 B2 | 4/2010 | Wang et al. | |
| 7,699,835 B2 | 4/2010 | Lee et al. | |
| 7,699,855 B2 | 4/2010 | Anderson et al. | |
| 7,778,733 B2 | 8/2010 | Nowlin et al. | |
| 7,819,884 B2 | 10/2010 | Lee et al. | |
| 7,819,885 B2 | 10/2010 | Cooper | |
| 7,862,579 B2 | 1/2011 | Ortiz et al. | |
| 7,865,266 B2 | 1/2011 | Moll et al. | |
| 7,955,321 B2 | 6/2011 | Kishi et al. | |
| 8,105,320 B2 | 1/2012 | Manzo | |
| 8,155,479 B2 * | 4/2012 | Hoffman et al. | 382/276 |
| 8,267,958 B2 | 9/2012 | Braun | |
| 8,350,806 B2 | 1/2013 | Nagasaka et al. | |
| 8,423,186 B2 | 4/2013 | Itkowitz et al. | |
| 8,496,647 B2 | 7/2013 | Blumenkranz et al. | |
| 8,540,748 B2 | 9/2013 | Murphy et al. | |
| 8,845,681 B2 | 9/2014 | Grace | |
| 8,876,858 B2 | 11/2014 | Braun | |
| 8,903,549 B2 | 12/2014 | Itkowitz et al. | |
| 8,906,002 B2 | 12/2014 | Kishi et al. | |
| 9,039,681 B2 | 5/2015 | Wang et al. | |
| 2001/0021859 A1 | 9/2001 | Kawai et al. | |
| 2001/0055062 A1 * | 12/2001 | Shioda et al. | 348/79 |
| 2002/0072736 A1 | 6/2002 | Tierney et al. | |
| 2002/0091374 A1 | 7/2002 | Cooper | |
| 2002/0128552 A1 | 9/2002 | Nowlin et al. | |
| 2003/0033024 A1 | 2/2003 | Sunaoshi | |
| 2003/0060927 A1 | 3/2003 | Gerbi et al. | |
| 2003/0069471 A1 * | 4/2003 | Nakanishi et al. | 600/101 |
| 2003/0083648 A1 | 5/2003 | Wang et al. | |
| 2003/0100817 A1 | 5/2003 | Wang et al. | |
| 2003/0216723 A1 | 11/2003 | Shinmura et al. | |
| 2004/0092912 A1 | 5/2004 | Jinno et al. | |
| 2004/0111113 A1 | 6/2004 | Nakamura et al. | |
| 2004/0140787 A1 | 7/2004 | Okamoto et al. | |
| 2004/0186345 A1 | 9/2004 | Yang et al. | |
| 2004/0186624 A1 | 9/2004 | Oda et al. | |
| 2004/0243147 A1 | 12/2004 | Lipow | |
| 2005/0020876 A1 * | 1/2005 | Shioda et al. | 600/101 |
| 2005/0021050 A1 | 1/2005 | Cooper | |
| 2005/0033117 A1 * | 2/2005 | Ozaki et al. | 600/109 |
| 2005/0125027 A1 | 6/2005 | Knodel et al. | |
| 2005/0149003 A1 | 7/2005 | Tierney et al. | |
| 2005/0228365 A1 | 10/2005 | Wang et al. | |
| 2005/0273086 A1 | 12/2005 | Green et al. | |
| 2006/0052664 A1 | 3/2006 | Julian et al. | |
| 2006/0074408 A1 | 4/2006 | Jinno et al. | |
| 2006/0079865 A1 | 4/2006 | Jinno et al. | |
| 2006/0079866 A1 | 4/2006 | Jinno et al. | |
| 2006/0087746 A1 | 4/2006 | Lipow | |
| 2006/0116973 A1 | 6/2006 | Okamoto et al. | |
| 2006/0149162 A1 | 7/2006 | Daw et al. | |
| 2006/0155262 A1 | 7/2006 | Kishi et al. | |
| 2006/0161138 A1 | 7/2006 | Orban, III et al. | |
| 2006/0190031 A1 | 8/2006 | Wales et al. | |
| 2006/0235436 A1 | 10/2006 | Anderson et al. | |
| 2007/0012135 A1 | 1/2007 | Tierney et al. | |
| 2007/0089557 A1 | 4/2007 | Solomon et al. | |
| 2007/0119274 A1 | 5/2007 | Devengenzo et al. | |
| 2007/0137372 A1 | 6/2007 | Devengenzo et al. | |
| 2007/0167679 A1 | 7/2007 | Miyamoto et al. | |
| 2007/0167680 A1 | 7/2007 | Miyamoto et al. | |

(56) References Cited

U.S. PATENT DOCUMENTS

| | | | |
|---|---|---|---|
| 2007/0173689 A1* | 7/2007 | Ozaki et al. | 600/111 |
| 2007/0197896 A1 | 8/2007 | Moll et al. | |
| 2007/0208375 A1 | 9/2007 | Nishizawa et al. | |
| 2007/0219668 A1 | 9/2007 | Takahashi et al. | |
| 2007/0225550 A1 | 9/2007 | Gattani et al. | |
| 2007/0249897 A1 | 10/2007 | Miyamoto et al. | |
| 2007/0265638 A1 | 11/2007 | Lipow et al. | |
| 2008/0015611 A1 | 1/2008 | Jinno et al. | |
| 2008/0033240 A1 | 2/2008 | Hoffman et al. | |
| 2008/0046122 A1 | 2/2008 | Manzo et al. | |
| 2008/0051631 A1 | 2/2008 | Dejima et al. | |
| 2008/0059131 A1 | 3/2008 | Tokita et al. | |
| 2008/0103524 A1 | 5/2008 | Grace | |
| 2008/0140088 A1 | 6/2008 | Orban, III | |
| 2008/0147091 A1 | 6/2008 | Cooper | |
| 2008/0177285 A1 | 7/2008 | Brock et al. | |
| 2008/0204425 A1 | 8/2008 | Nagasaka et al. | |
| 2008/0215065 A1 | 9/2008 | Wang et al. | |
| 2008/0228196 A1 | 9/2008 | Wang et al. | |
| 2008/0234866 A1* | 9/2008 | Kishi et al. | 700/259 |
| 2008/0243142 A1* | 10/2008 | Gildenberg | 606/130 |
| 2008/0287735 A1 | 11/2008 | Takemoto et al. | |
| 2008/0312668 A1 | 12/2008 | Grace | |
| 2009/0018700 A1 | 1/2009 | Okamoto et al. | |
| 2009/0022262 A1* | 1/2009 | Ohishi | 378/4 |
| 2009/0030273 A1 | 1/2009 | Murakami | |
| 2009/0034820 A1* | 2/2009 | Sugiyama | 382/132 |
| 2009/0036736 A1 | 2/2009 | Dejima et al. | |
| 2009/0036902 A1* | 2/2009 | DiMaio et al. | 606/130 |
| 2009/0046146 A1* | 2/2009 | Hoyt | 348/143 |
| 2009/0057369 A1 | 3/2009 | Smith et al. | |
| 2009/0088634 A1* | 4/2009 | Zhao et al. | 600/427 |
| 2009/0088773 A1* | 4/2009 | Zhao et al. | 606/130 |
| 2009/0088897 A1* | 4/2009 | Zhao et al. | 700/250 |
| 2009/0163948 A1 | 6/2009 | Sunaoshi et al. | |
| 2009/0171147 A1 | 7/2009 | Lee et al. | |
| 2009/0182193 A1 | 7/2009 | Whitman et al. | |
| 2009/0193299 A1 | 7/2009 | Sekiguchi et al. | |
| 2009/0204911 A1 | 8/2009 | Sekiguchi et al. | |
| 2009/0247877 A1* | 10/2009 | Tanaka et al. | 600/462 |
| 2009/0326318 A1 | 12/2009 | Tognaccini et al. | |
| 2010/0010673 A1* | 1/2010 | Wang et al. | 700/264 |
| 2010/0013812 A1 | 1/2010 | Gu et al. | |
| 2010/0087835 A1 | 4/2010 | Blumenkranz et al. | |
| 2010/0163057 A1 | 7/2010 | Anderson et al. | |
| 2010/0174293 A1 | 7/2010 | Orban, III et al. | |
| 2010/0217284 A1 | 8/2010 | Grace | |
| 2010/0217528 A1 | 8/2010 | Sato et al. | |
| 2010/0228264 A1 | 9/2010 | Robinson et al. | |
| 2010/0228265 A1 | 9/2010 | Prisco | |
| 2010/0234857 A1 | 9/2010 | Itkowitz et al. | |
| 2010/0274087 A1 | 10/2010 | Diolaiti et al. | |
| 2010/0291520 A1 | 11/2010 | Kurenov et al. | |
| 2010/0317965 A1* | 12/2010 | Itkowitz et al. | 600/425 |
| 2010/0318099 A1* | 12/2010 | Itkowitz et al. | 606/130 |
| 2010/0318101 A1 | 12/2010 | Choi | |
| 2010/0332031 A1 | 12/2010 | Itkowitz et al. | |
| 2011/0015650 A1 | 1/2011 | Choi et al. | |
| 2011/0050852 A1* | 3/2011 | Lamprecht et al. | 348/43 |
| 2011/0118707 A1* | 5/2011 | Burbank | 606/1 |
| 2011/0118748 A1 | 5/2011 | Itkowitz | |
| 2011/0118753 A1 | 5/2011 | Itkowitz et al. | |
| 2011/0137337 A1 | 6/2011 | van den Dool et al. | |
| 2011/0230894 A1 | 9/2011 | Simaan et al. | |
| 2011/0238079 A1* | 9/2011 | Hannaford et al. | 606/130 |
| 2011/0282493 A1 | 11/2011 | Ortmaier | |
| 2011/0288579 A1 | 11/2011 | Hyodo | |
| 2012/0165828 A1 | 6/2012 | Duque et al. | |
| 2012/0191245 A1 | 7/2012 | Fudaba et al. | |

FOREIGN PATENT DOCUMENTS

| | | |
|---|---|---|
| EP | 0 677 278 A1 | 10/1995 |
| EP | 1 728 475 A2 | 12/2006 |
| EP | 2 092 875 A1 | 8/2009 |
| EP | 2 298 220 A1 | 3/2011 |
| EP | 2 332 484 A2 | 6/2011 |
| JP | 63-029810 A | 2/1988 |
| JP | 64-034688 A | 2/1989 |
| JP | 01-271185 A | 10/1989 |
| JP | 02-071980 A | 3/1990 |
| JP | 02-292193 A | 12/1990 |
| JP | 03-161289 A | 7/1991 |
| JP | 05-096477 A | 4/1993 |
| JP | 5-329784 A | 12/1993 |
| JP | 07-001366 A | 1/1995 |
| JP | 07-194609 A | 8/1995 |
| JP | 07-241300 A | 9/1995 |
| JP | 07-246578 A | 9/1995 |
| JP | 07-096182 B2 | 10/1995 |
| JP | 8-66883 A | 3/1996 |
| JP | 08-215204 A | 8/1996 |
| JP | 08-243080 A | 9/1996 |
| JP | 10-128538 A | 5/1998 |
| JP | 11-300662 A | 11/1999 |
| JP | 2000-312684 A | 11/2000 |
| JP | 2001-087281 A | 4/2001 |
| JP | 2001-113481 A | 4/2001 |
| JP | 2001-277157 A | 10/2001 |
| JP | 2001-309920 A | 11/2001 |
| JP | 2002-014287 A | 1/2002 |
| JP | 2002-059380 A | 2/2002 |
| JP | 2002-102248 A | 4/2002 |
| JP | 2002-272758 A | 9/2002 |
| JP | 2002-537884 A | 11/2002 |
| JP | 2003-024336 A | 1/2003 |
| JP | 2003-053685 A | 2/2003 |
| JP | 2003-250812 A | 9/2003 |
| JP | 2003-265500 A | 9/2003 |
| JP | 2003-340752 A | 12/2003 |
| JP | 2004-105451 A | 4/2004 |
| JP | 2005-511185 A | 4/2005 |
| JP | 2005-192743 A | 7/2005 |
| JP | 3686947 B2 | 8/2005 |
| JP | 2005-261827 A | 9/2005 |
| JP | 2005-312991 A | 11/2005 |
| JP | 2006-061272 A | 3/2006 |
| JP | 2006-167867 A | 6/2006 |
| JP | 2006-288955 A | 10/2006 |
| JP | 2006-321027 A | 11/2006 |
| JP | 2007-029274 A | 2/2007 |
| JP | 2007-038315 A | 2/2007 |
| JP | 2007-98507 A | 4/2007 |
| JP | 2007-105485 A | 4/2007 |
| JP | 3999816 B2 | 10/2007 |
| JP | 2008-000282 A | 1/2008 |
| JP | 2008-036793 A | 2/2008 |
| JP | 4058113 B2 | 3/2008 |
| JP | 2008-93270 A | 4/2008 |
| JP | 2008-173724 A | 7/2008 |
| JP | 4129313 B | 8/2008 |
| JP | 4176126 B2 | 11/2008 |
| JP | 2009-028157 A | 2/2009 |
| JP | 2009-056164 A | 3/2009 |
| JP | 2009-512514 A | 3/2009 |
| JP | 2009-520573 A | 5/2009 |
| JP | 2009-178230 A | 8/2009 |
| JP | 2009-178541 A | 8/2009 |
| JP | 2009-530037 A | 8/2009 |
| JP | 2009-195694 A | 9/2009 |
| JP | 2009-226093 A | 10/2009 |
| JP | 2009-269127 A | 11/2009 |
| JP | 2010-504127 A | 2/2010 |
| JP | 2010-076012 A | 4/2010 |
| JP | 2010-524548 A | 7/2010 |
| JP | 2011-509112 A | 3/2011 |
| JP | 2011-206213 A | 10/2011 |
| JP | 2012-012104 A | 1/2012 |
| JP | 2012-091310 A | 5/2012 |
| WO | 97/16123 A1 | 5/1997 |
| WO | 97/16124 A1 | 5/1997 |
| WO | 97/29690 A1 | 8/1997 |
| WO | 98/25666 A1 | 6/1998 |

(56) References Cited

FOREIGN PATENT DOCUMENTS

| | | |
|---|---|---|
| WO | WO 00/51486 A1 | 9/2000 |
| WO | 00/60421 A2 | 10/2000 |
| WO | WO 03/049596 A2 | 6/2003 |
| WO | 2006/111966 A2 | 10/2006 |
| WO | WO 2007/047782 A2 | 4/2007 |
| WO | WO 2007/075864 A1 | 7/2007 |
| WO | WO 2007/111955 A2 | 10/2007 |
| WO | WO 2007/126443 A2 | 11/2007 |
| WO | WO 2007/138674 A1 | 12/2007 |
| WO | WO 2008/038184 A2 | 4/2008 |
| WO | WO 2008/108289 A1 | 9/2008 |
| WO | WO 2009034477 A2 | 3/2009 |
| WO | 2009/089614 A1 | 7/2009 |
| WO | WO 2010006057 A1 | 1/2010 |
| WO | WO 2010109932 A1 | 9/2010 |
| WO | 2011/025786 A1 | 3/2011 |
| WO | 2011/060139 A2 | 5/2011 |
| WO | 2011/060185 A1 | 5/2011 |
| WO | 2011/085815 A1 | 7/2011 |
| WO | WO 2012/042949 A1 | 4/2012 |

OTHER PUBLICATIONS

English Abstract of WO 0051486 A1 dated Sep. 8, 2000.
International Search Report dated Oct. 23, 2012 issued in PCT/JP2012/070414.
International Search Report dated Sep. 4, 2012 issued in PCT/JP2012/070408.
International Search Report dated Aug. 28, 2012 issued in PCT/JP2012/069927.
International Search Report dated Sep. 4, 2012 issued in PCT/JP2012/070415.
International Search Report dated Oct. 16, 2012 issued in PCT/JP2012/070581.
International Search Report dated Nov. 13, 2012 issued in PCT/JP2012/070576.
International Search Report dated Sep. 18, 2012 issued in PCT/JP2012/070417.
International Search Report dated Oct. 30, 2012 issued in PCT/JP2012/070418.
International Search Report dated Sep. 11, 2012 issued in PCT/JP2012/070416.
International Search Report dated Sep. 18, 2012 issued in PCT/JP2012/070407.
International Search Report dated Sep. 18, 2012 issued in PCT/JP2012/069868.
International Search Report dated Nov. 6, 2012 issued in PCT/JP2012/069919.
International Search Report dated Sep. 11, 2012 issued in PCT/JP2012/069696.
U.S. Office Action dated May 8, 2015 from related U.S. Appl. No. 14/157,920.
Notice of Allowance dated Jan. 20, 2015 from related U.S. Appl. No. 13/566,023.
Extended Supplementary European Search Report dated Feb. 12, 2015 from related European Application No. 12 81 9447.9.
Extended Supplementary European Search Report dated Feb. 13, 2015 from related European Application No. 12 82 0679.4.
Supplementary European Search Report dated Feb. 18, 2015 from related European Application No. 12 82 0758.6.
Extended Supplementary European Search Report dated Feb. 23, 2015 from related European Application No. 12 81 9877.7.
Extended Supplementary European Search Report dated Feb. 23, 2015 from related European Application No. 12 82 0239.7.
Partial Supplementary European Search Report dated Feb. 26, 2015 from related European Application No. 12 82 0666.4.
Partial Supplementary European Search Report dated Feb. 27, 2015 from related European Application No. 12 81 9672.2.
Extended Supplementary European Search Report dated Mar. 2, 2015 from related European Application No. 12 82 0017.7.
Extended Supplementary European Search Report dated Mar. 16, 2015 from related European Application No. 12 82 0479.9.
Extended Supplementary European Search Report dated Mar. 16, 2015 from related European Application No. 12 81 9504.7.
Extended Supplementary European Search Report dated Mar. 16, 2015 from related European Application No. 12 81 9398.4.
Office Action dated Mar. 25, 2015 received in related U.S. Appl. No. 14/169,321.
Extended Supplementary European Search Report dated Mar. 27, 2015 from related European Application No. 12 82 0056.5.
Office Action dated Apr. 9, 2015 received in related U.S. Appl. No. 14/169,675.
Extended Supplementary European Search Report dated Jul. 1, 2015 from related European Application No. 12 82 0066.4.
Extended Supplementary European Search Report dated Jul. 2, 2015 from related European Application No. 12 81 9672.2.
Office Action dated Sep. 16, 2015 received in related U.S. Appl. No. 13/566,012.
Office Action dated Oct. 19, 2015 received in related U.S. Appl. No. 14/168,525.

* cited by examiner

SURGICAL ASSISTANT SYSTEM

This application is a continuation application based on PCT Patent Application No. PCT/JP2012/070581, filed Aug. 6, 2012, claiming priority based on U.S. Patent Provisional Application No. 61/515,203 filed on Aug. 4, 2011 and Japanese Patent Application No. 2012-043487 filed on Feb. 29, 2012, the contents of which are incorporated herein by reference.

BACKGROUND OF THE INVENTION

1. Field of the Invention

The present invention relates to a surgical assistant system.

2. Description of the Related Art

Conventionally, various surgical assistant systems have been developed in order to allow surgeons to easily perform surgery on patients.

For example, a surgical microscope device is disclosed in Japanese Unexamined Patent Application, First Publication No. 2002-14287. In the surgical microscope device of Japanese Unexamined Patent Application, First Publication No. 2002-14287, operation switches are disposed in a scope holder that holds an endoscope. These operation switches cause the usage state of the device to be detected via the scope holder, and cause an endoscopic image or an endoscope observation image to be switched and displayed on a microscope viewing field (display unit). According to the configuration of the surgical microscope device of Japanese Unexamined Patent Application, First Publication No. 2002-14287, it is possible to reduce the fatigue of the surgeon or to shorten the surgery time. In addition, it is possible for the surgeon to move the scope holder without moving the line of sight in the surgical microscope device of Japanese Unexamined Patent Application, First Publication No. 2002-14287.

In addition, generally, in a master-slave type surgical assistant system using an arm or a manipulator, the surgeon operating the arm of a master side sits in front of the console, and operates the arm while watching an immersive type monitor (display unit) displaying an image from the endoscope disposed in the console. According to this operation, the surgeon moves an arm of a slave side that treats the patient.

A plurality of arms or footswitches that are input devices are disposed in the console. The plurality of footswitches, for example, switches an operation mode of the system, and controls an output of a surgical energy device such as an electric scalpel mounted on the arm.

SUMMARY OF THE INVENTION

According to a first aspect of the present invention, a surgery support device includes an operation unit, an arm unit, an operation imaging unit, an endoscope, a mode control unit, a driving unit, a synthetic image creation unit, and a display unit. The operation unit gives an input. A treatment tool is mounted on the arm unit. The operation imaging unit acquires an operation image that is an image including the operation unit. The endoscope acquires an internal-body image including an image of an interior of a body of a patient. The mode control unit is configured to have a plurality of operation modes and to enable one of the plurality of operation modes to be set as a setting operation mode. The driving unit is configured to enable the arm unit to be operated based on the input given by the operation unit and the setting operation mode. The synthetic image creation unit synthesizes images using at least the operation image to create a synthetic image based on the setting operation mode. The display unit displays the synthetic image.

According to a second aspect of the present invention, in the surgical assistant system according to the first aspect, the surgical assistant system may further include a mode switching unit configured to switch the operation mode. In the surgical assistant system, the operation mode may include a ready mode and a driving mode. In the ready mode, the arm unit may be in a state before being operatable by the operation unit, and the synthetic image creation unit creates the synthetic image including the operation image. In the driving mode, the driving unit may be capable of operating the arm unit based on the input given by the operation unit and the synthetic image creation unit creates the synthetic image including the operation image and the internal-body image. The mode switching unit may switch the operation mode set as the setting operation mode between the ready mode and the driving mode by transmitting a signal to the mode control unit.

According to a third aspect of the present invention, in the surgical assistant system according to the first aspect, the surgical assistant system may further include an arm imaging unit configured to acquire an arm image that is an image including the arm unit. The synthetic image creation unit may create the synthetic image by synthesizing images using the arm image.

According to a fourth aspect of the present invention, in the surgical assistant system according to the second aspect, the surgical assistant system may further include an arm imaging unit configured to acquire an arm image that is an image including the arm unit. The synthetic image creation unit may create the synthetic image by synthesizing images using the arm image.

According to a fifth aspect of the present invention, in the surgical assistant system according to the fourth aspect, the surgical assistant system may further include a positioning switching unit configured to switch the operation mode. In the surgical assistant system, the ready mode may include a standby mode and a positioning mode. In the standby mode, the arm unit may be in a standby state in which the arm unit waits in a state before being operatable by the operation unit, and the synthetic image creation unit creates the synthetic image including the operation image. In the positioning mode, a position of the arm unit may be capable of being adjusted, and the synthetic image creation unit creates the synthetic image including the operation image and the arm image. The positioning switching unit may switch the operation mode set as the setting operation mode between the standby mode and the positioning mode by transmitting a signal to the mode control unit.

According to a sixth aspect of the present invention, in the surgical assistant system according to the fourth aspect, the surgical assistant system may further include a standby exchange switching unit configured to switch the operation mode. In the surgical assistant system, the arm unit may be configured to enable the treatment tool to be detachable. The ready mode may include a standby mode and a standby surgical device exchange mode. In the standby mode, the arm unit may be in a standby state in which the arm unit waits in a state before being operatable by the operation unit, and the synthetic image creation unit may create the synthetic image including the operation image. In the standby surgical device exchange mode, the arm unit may be capable of being operated by the operation unit, and the synthetic image creation unit may create the synthetic image including the operation image, the internal-body image, and the arm image in a state in which the treatment tool can be exchanged. The standby exchange switching unit may switch the operation mode set as the setting operation mode between the standby mode and the standby surgical device exchange mode by transmitting a signal to the mode control unit.

According to a seventh aspect of the present invention, in the surgical assistant system according to the sixth aspect, the synthetic image creation unit may create the synthetic image in which the operation image and the internal-body image may be disposed at an edge of the arm image in the standby surgical device exchange mode.

According to an eighth aspect of the present invention, in the surgical assistant system according to the fourth aspect, the surgical assistant system may further include an emergency stop switching unit. In the surgical assistant system, the ready mode may include a standby mode and an emergency stop mode. In the standby mode, the arm unit may be in a standby state in which the arm unit waits in a state before being operatable by the operation unit, and the synthetic image creation unit may create the synthetic image including the operation image. In the emergency stop mode, an operation of the arm unit may be forcibly stopped, and the synthetic image creation unit may create the synthetic image including the operation image, the internal-body image, and the arm image. The emergency stop switching unit may switch the operation mode set as the setting operation mode between the standby mode and the emergency stop mode by transmitting a signal to the mode control unit.

According to a ninth aspect of the present invention, in the surgical assistant system according to any one of the fourth to eighth aspects, the surgical assistant system may further include a driving exchange switching unit. In the surgical assistant system, the arm unit may enable the treatment tool to be detachable. The driving mode may include a driving normal surgical device mode and a driving surgical device exchange mode. In the driving normal surgical device mode, the synthetic image creation unit may create the synthetic image using the operation image and the internal-body image in a state in which the arm unit is operated by the operation unit. In the driving surgical device exchange mode, the arm unit may be capable of being operated by the operation unit, and the synthetic image creation unit may create the synthetic image including the operation image, the internal-body image, and the arm image in a state in which the treatment tool can be exchanged. The driving exchange switching unit may switch the operation mode set as the setting operation mode between the driving normal surgical device mode and the driving surgical device exchange mode by transmitting a signal to the mode control unit.

According to a tenth aspect of the present invention, in the surgical assistant system according to the ninth to eighth aspect, the synthetic image creation unit may create the synthetic image in which the operation image and the arm image are disposed at an edge of the internal-body image in the driving treatment exchange mode.

According to a eleventh aspect of the present invention, in the surgical assistant system according to any one of the fourth to eighth aspects, the surgical assistant system may further include an electric energy switching imaging unit configured to be a part of the operation imaging unit and a driving electric mode switching unit configured to switch the operation mode. In the surgical assistant system, the treatment tool may divide into a nonelectric type surgical device that does not use electric energy and an electric type surgical device that uses electric energy. The operation unit may have an electric energy switching unit switching whether or not the electric energy is supplied to the electric type surgical device as a part of the operation unit. The electric energy switching imaging unit may acquire an electric energy switching image that is an image including the electric energy switching unit. The electric energy switching imaging unit may be configured as a part of the operation imaging unit. The operation image may include the electric energy switching image. The driving mode may include a driving normal surgical device mode and a driving electricity treatment tool mode. In the driving normal surgical device mode, the synthetic image creation unit may create the synthetic image using the operation image and the internal-body image in a state in which the arm unit is operated by the operation unit. In the driving electricity treatment tool mode, the synthetic image creation unit may create the synthetic image including the internal-body image and the electric energy switching image. The driving electric mode switching unit may switch the operation mode set as the setting operation mode between the driving normal surgical device mode and the driving electricity treatment tool mode by transmitting a signal to the mode control unit.

DETAILED DESCRIPTION OF THE INVENTION

Hereinafter, a surgical assistant system according to one embodiment of the present invention will be described with reference to FIGS. 1 to 13. Hereinafter, for example, a case in which the surgical assistant system is a master-slave type surgical assistant system will be described. The master-slave type surgical assistant system includes master arms 11A and 11B and slave arms 21A to 21D that will be described later. The master-slave type surgical assistant system is a device that remotely controls the slave arms 21A to 21D so as to follow operations of the master arms 11A and 11B to which the input is given by the surgeon.

Figure 1:
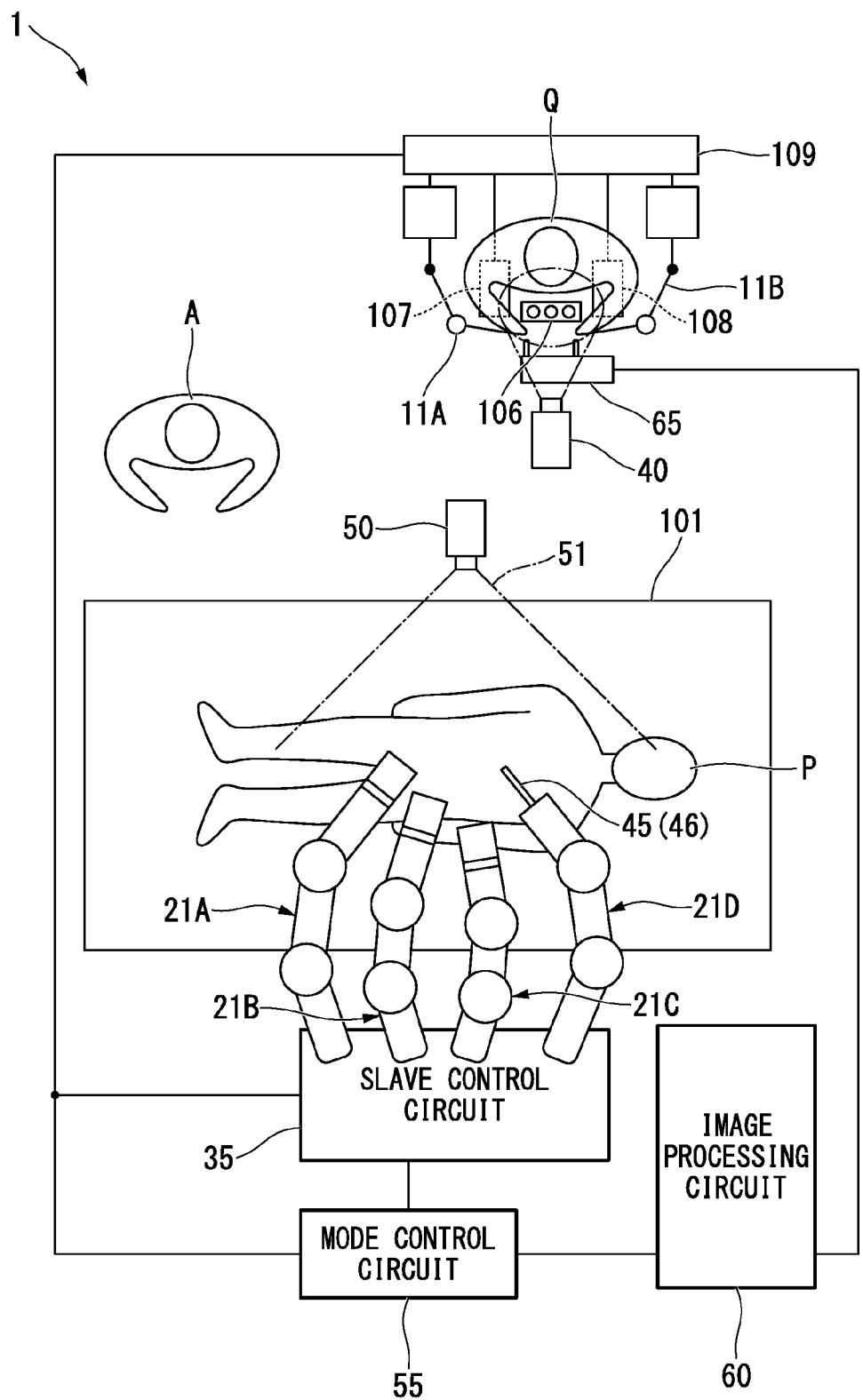
FIG. 1 is a plan view schematically illustrating a surgical assistant system in accordance with one embodiment of the present invention.
Figure 2:
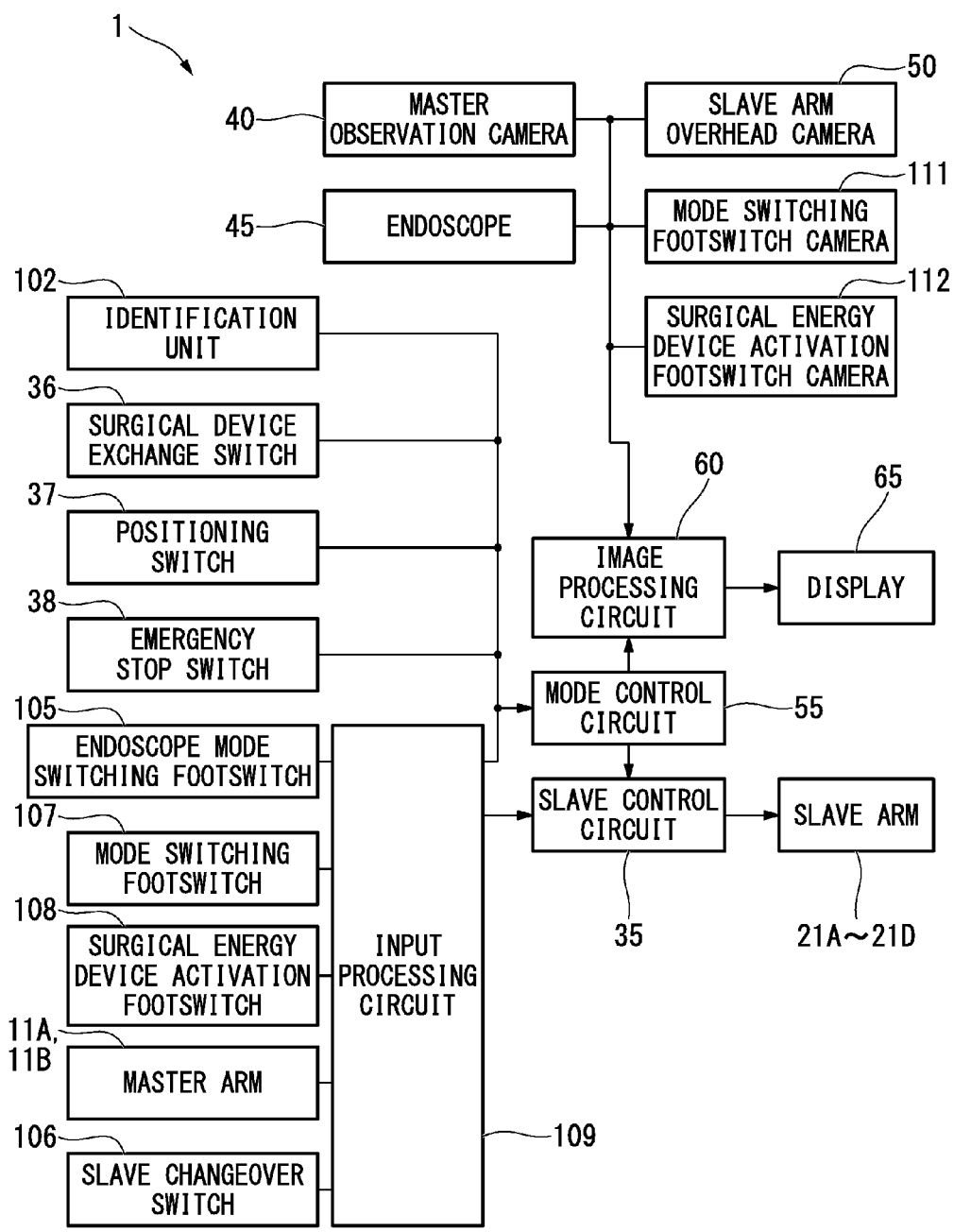
FIG. 2 is a block diagram illustrating the surgical assistant system in accordance with the embodiment of the present invention.

As shown in FIGS. 1 and 2, the surgical assistant system 1 includes the master arms 11A and 11B, four slave arms 21A to 21D (arm unit), a slave control circuit 35 (driving unit) capable of driving the slave arms 21A to 21D, a master observation camera 40 acquiring an operation image that is an image including the master arms 11A and 11B, an endoscope 45 capable of observing the interior of a body of a patient P, a slave arm overhead camera 50 (arm imaging unit) acquiring an arm image that is an image including the slave arms 21A to 21D, a mode control circuit 55 (mode control unit) having a plurality of operation modes, an image processing circuit 60 (synthetic image creation unit) creating a synthetic image from the operation image and the arm image in response to the operation mode, and a display 65 (display unit) displaying the synthetic image.

In addition, since the master arms 11A and 11B have the same configuration, their symbols have common reference numerals. Since the slave arms 21A to 21D also have the same configuration except a part of the slave arm 21D, their symbols also have common reference numerals. For example, in the configuration of the slave arm 21A, letter "A" is added to the reference numeral. In the configuration of the slave arm 21B, letter "B" is added to the reference numeral.

First, a configuration of each operation mode of the mode control circuit 55 will be described.

Figure 3:
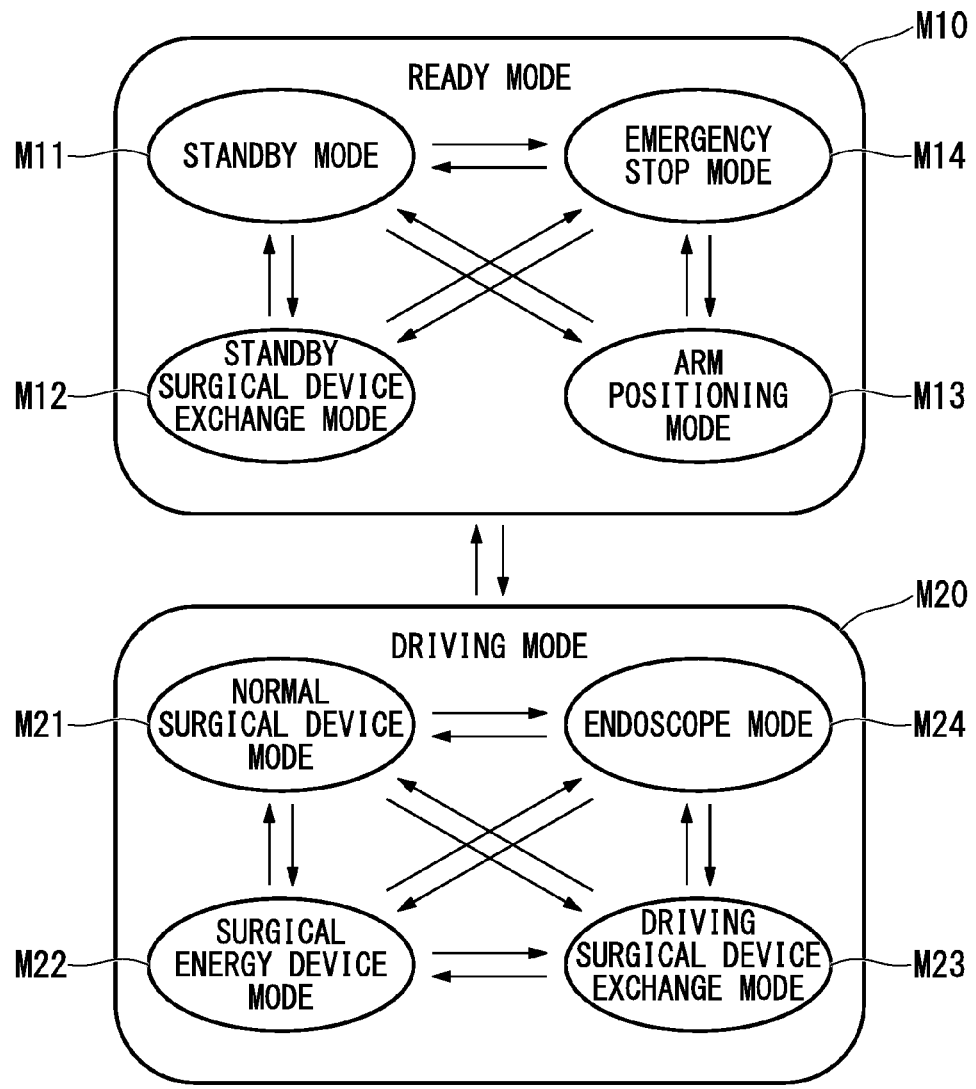
FIG. 3 is a diagram illustrating operation modes of a mode control circuit of the surgical assistant system in accordance with the embodiment of the present invention.

As shown in FIG. 3, the operation mode is mainly divided into a ready mode M10 and a driving mode M20. In the ready mode M10, the slave arms 21A to 21D wait in a state before being operatable by the master arms 11A and 11B. That is, the ready mode M10 is a mode in which the slave arms 21A to 21D are not operated by the slave control circuit 35 even when the master arms 11A and 11B are operated. On the other hand, the driving mode M20 is a mode in which the slave control circuit 35 causes some of the slave arms 21A to 21D to follow the input and operate based on the input given to the master arms 11A and 11B. Operations of the master arms 11A and 11B include operations (e.g., operations to open or close a pair of grasping pieces of the distal ends of the treatment tool) of the treatment tools mounted on the slave arms 21A to 21D via the grasping units 12A and 12B (see FIG. 5) disposed at distal ends of the master arms 11A and 11B.

The ready mode M10 includes a standby mode M11, a standby surgical device exchange mode M12, an arm positioning mode (positioning mode) M13, and an emergency stop mode M14. Meanwhile, the driving mode M20 includes a normal surgical device mode (driving normal surgical device mode) M21, a surgical energy device mode (driving electricity treatment tool mode) M22, a driving surgical device exchange mode M23, and an endoscope mode M24.

Details of the modes will be described later, and switching between the modes may be performed as follows. In addition, any mode included in the driving mode M20 is switched to any mode included in the ready mode M10. Similarly, any mode included in the ready mode M10 is switched to any mode included in the driving mode M20.

Within the ready mode M10, the setting operation mode is arbitrarily switched between the standby mode M11, the standby surgical device exchange mode M12, the arm positioning mode M13, and the emergency stop mode M14 except for the case between the standby surgical device exchange mode M12 and the arm positioning mode M13. Within the driving mode M20, the setting operation mode is arbitrarily switched between the normal surgical device mode M21, the surgical energy device mode M22, the driving surgical device exchange mode M23, and the endoscope mode M24.

The description will continue with reference to FIGS. 1 and 2.

The patient P is observed and treated while being loaded on the surgical table 101. The slave arms 21A and 21D are disposed near the surgical table 101.

Figure 4:
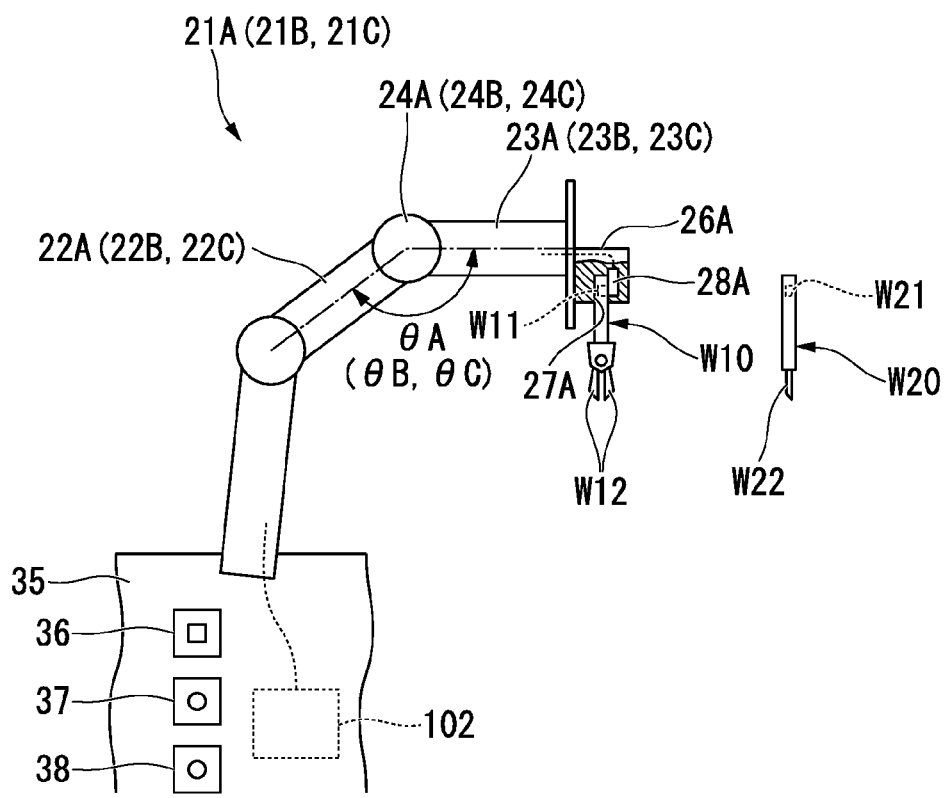
FIG. 4 is a diagram illustrating a slave arm of the surgical assistant system in accordance with the embodiment of the present invention.

Although the slave arm 21A is configured to generally have multi-degree-of-freedom joints, hereinafter, elements of some of the slave arms 21A to 21D are focused on and described for simplicity of description. That is, when each of the slave arms 21A to 21D has one joint, a case in which the slave arm 21A has a proximal end side support shaft (proximal end side support) 22A, a distal end side support shaft (distal end support) 23A, and a joint unit 24A as shown in FIG. 4 will be basically described. The proximal end side support shaft 22A is fixed to a housing case of the slave control circuit 35. The joint unit 24A connects the proximal end side support shaft 22A and the distal end side support shaft 23A.

A holding unit 26A that is slidable in a direction orthogonal to the longitudinal direction of the distal end side support shaft 23A is disposed at the distal end portion of the distal end side support shaft 23A. An insertion hole 27A is formed in the holding unit 26A. A pair of arm side electrodes 28A are exposed and disposed within the insertion hole 27A. The insertion hole 27A is configured to enable the treatment tool such as a grasping forceps W10 or a high-frequency electric knife W20 that will be described later to be detachable.

The treatment tool is divided into a nonelectric type surgical device such as the grasping forceps W10 that does not use the electric energy and an electric type surgical device such as the high-frequency electric knife W20 that does use electric energy. An electric resistor (first identification unit) W11 is disposed in the grasping forceps W10 while a pair of treatment tool side electrodes is exposed. A pair of grasping pieces W12 is disposed at the distal end side of the grasping forceps W10.

An electric resistor (second identification unit) W21 having a different resistance value (electrical property) from the electric resistor W11 is disposed in the high-frequency electric knife W20 while the pair of treatment tool side electrodes are exposed. A knife W22 is disposed at the distal end portion of the high-frequency electric knife W20.

When the proximal end portion of the grasping forceps W10 is inserted into the insertion hole 27A, the arm side electrode 28A of the holding unit 26A and the treatment tool side electrode of the grasping forceps W10 are electrically connected to each other. In this case, a constant voltage is applied between the arm side electrodes 28A to measure the resistance value of the electric resistor W11 by virtue of the identification unit 102. Further, the pair of grasping pieces W12 are moved toward each other or spaced apart from each other by operating the slave arm 21A using a mechanism and a power unit that is built in the slave arm 21A but not shown. A so-called opening and closing operation for the pair of grasping pieces W12 is possible. The power unit mentioned above, for example, may use a servo motor.

When the proximal end portion of the high-frequency electric knife W20 is inserted into the insertion hole 27A, the arm side electrode 28A of the holding unit 26A and the treatment tool side electrode of the high-frequency electric knife W20 are electrically connected to each other. In this case, a resistance value of the electric resistor W21 is measured by the identification unit 102. Further, a high-frequency current (electric energy) may be supplied to the high-frequency electric knife W20 from the slave arm 21A side by an electrode that is not shown.

In this way, it is possible for the identification unit 102 to detect which of the electric resistor W11 and the electric resistor W21 the treatment tool mounted on the holding unit 26A has by measuring the resistance value. The identification unit 102 transmits a signal indicating the kind of the detected treatment tool to the mode control circuit 55.

The joint unit 24A has an electromagnetic clutch, a power unit, and so forth that are not shown. The power unit, for example, may include a motor (a servo motor) equipped with the servomechanism having an incremental encoder or a decelerator. By transmitting the control signal to the joint unit 24A and supplying electric energy to the joint unit 24A from the slave control circuit 35, it is possible for the joint unit 24A to adjust an arrangement angle θA formed between the proximal end side support shaft 22A and the distal end side support shaft 23A to a desired value.

For example, the slave control circuit 35 is configured to have a CPU or a memory in which a control program is stored. In addition, by detecting the arrangement angle θA when the helper (assistant doctor or nurse) and the like that will be described later has adjusted the position of the distal end side support shaft 23A, the slave control circuit 35 can store the adjusted arrangement angle θA in the memory as an initial position of the slave arm 21A.

In addition, the slave arm 21D on which the endoscope 45 is detachably mounted as described above has the same configuration (not shown) as the slave arm 21A except for the holding unit 26A. The holding unit of the slave arm 21D is configured to allow the endoscope 45 to be mounted.

The slave control circuit 35 also controls the power unit that is built in the slave arm 21A. The slave control circuit 35 selects all or some of the slave arms 21A to 21D by designating a slave changeover switch 106 that will be described later. Further, the slave control circuit 35 can follow the input given to the master arms 11A and 11B and be driven based on the setting operation mode set by the mode control circuit 55.

A surgical device exchange switch (standby exchange switching unit and driving exchange switching unit) 36, a positioning switch (positioning switching unit) 37, and an emergency stop switch (emergency stop switching unit) 38 are disposed in the slave control circuit 35.

As shown in FIG. 2, the surgical device exchange switch 36, the positioning switch 37, and the emergency stop switch 38 are connected to the mode control circuit 55.

A signal is transmitted to the mode control circuit 55 by operating the surgical device exchange switch 36.

The mode control circuit 55 switches the setting operation mode to the standby surgical device exchange mode M12 based on the signal while the current setting operation mode is any mode within the ready mode M10 based on the signal. In addition, when the current setting operation mode is any mode within the driving mode M20, the mode control circuit switches the setting operation mode to the driving surgical device exchange mode M23.

A signal is transmitted to the mode control circuit 55 by operating the positioning switch 37, and the setting operation mode is then switched to the arm positioning mode M13. A signal is transmitted to the mode control circuit 55 by operating the emergency stop switch 38, and the setting operation mode is then switched to the emergency stop mode M14.

The slave control circuit 35 can position the grasping forceps W10 mounted on the holding unit 26A with respect to the patient P loaded on the surgical table 101 by adjusting the arrangement angle θA formed by the joint unit 24A of the slave arm 21A.

As shown in FIG. 1, the viewing range 51 of the slave arm overhead camera 50 mentioned above is set such that an entire image of the slave arms 21A to 21D driven in this way can be acquired. The slave arm overhead camera 50 may be disposed to look down upon the entire surgical room as well as the slave arms 21A to 21D.

Although the master arm 11A is configured to be smaller than the slave arm 21A, the master arm 11A basically has a similar configuration to the slave arm 21A. That is, the master arm 11A has a configuration in which a sensor (such as an incremental encoder) detecting the arrangement angle formed by the support shaft is disposed between the pair of support shafts.

Figure 5:
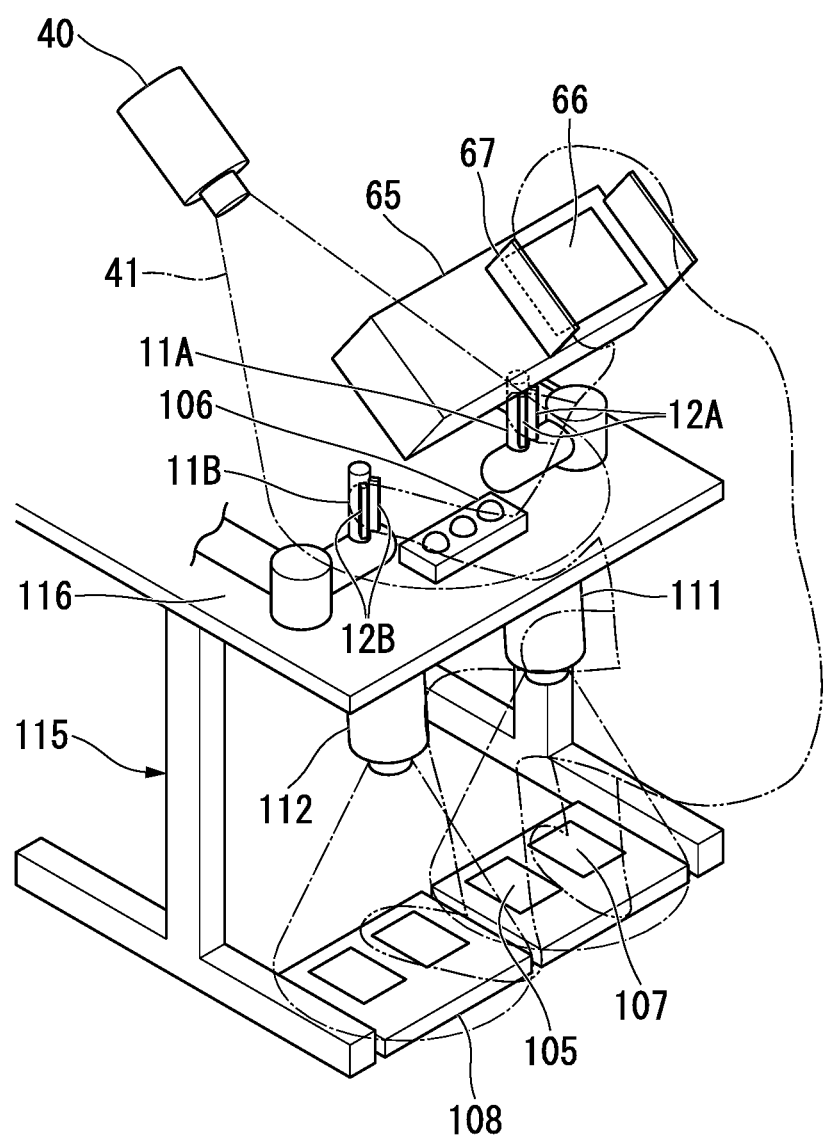
FIG. 5 is a perspective view illustrating a periphery of an operation desk of the surgical assistant system in accordance with the embodiment of the present invention.

As shown in FIG. 5, the viewing range 41 of the master observation camera 40 mentioned above is set such that the images of the master arms 11A and 11B can be acquired.

The slave changeover switch 106 for switching the slave arms 21A to 21D operated by the master arms 11A and 11B, an endoscope mode switching footswitch 105, a mode switching footswitch 107 (mode switching unit and driving electric mode switching unit), a surgical energy device activation footswitch 108 (electric energy switching unit), and the display 65 are disposed near the master arms 11A and 11B. In addition, the operation unit is configured to include the master arms 11A and 11B, the endoscope mode switching footswitch 105, the mode switching footswitch 107, and the surgical energy device activation footswitch 108.

As shown in FIG. 2, the master arms 11A and 11B, the slave changeover switch 106, the mode switching footswitch 107, and the surgical energy device activation footswitch 108 are connected to an input processing circuit 109. The input processing circuit 109 is used to collect wires for signals to be transmitted from the master arms 11A and 11B sides to the slave arms 21A to 21D sides. The input processing circuit 109 has a known configuration. An angle detected by the sensors of the master arms 11A and 11B and signals transmitted from the slave changeover switch 106 and the surgical energy device activation footswitch 108 are transmitted to the slave control circuit 35 via the input processing circuit 109. On the other hand, signals transmitted from the endoscope mode switching footswitch 105 and the mode switching footswitch 107 are transmitted to the mode control circuit 55 via the input processing circuit 109.

The slave changeover switch 106 can set the slave arm to be operated by the slave control circuit 35 among the slave arms 21A to 21D.

The setting operation mode is in the standby mode M11 right after a power is supplied. The signal is transmitted from the mode switching footswitch 107 to the mode control circuit 55 by operating the mode switching footswitch 107. When the signal is transmitted, the operation mode set to the setting operation mode is switched to the standby mode M11, the normal surgical device mode M21, or the surgical energy device mode M22. When the endoscope mode switching footswitch 105 is operated, the operation mode set to the setting operation mode is switched to the endoscope mode M24. It is possible to adjust the amount of the high-frequency current to be supplied by operating the surgical energy device activation footswitch 108 to switch whether or not the high-frequency current is supplied to the high-frequency electric knife W20 mounted on the slave arm selected by the slave changeover switch 106 among the holding units 26A to 26C of the respective slave arms 21A to 21C.

As the display 65, an immersive type monitor in which a display surface 66 is more recessed than an outer surface of the main body 67 is used. A liquid crystal panel or the like may be properly used for the display surface 66. The display 65 displays an image on the display surface 66 which is converted from the signal transmitted from the image processing circuit 60 which will be described later by a circuit (not shown).

In order to acquire an image including the mode switching footswitch 107 and the endoscope mode switching footswitch 105, a mode switching footswitch camera 111 is disposed above the mode switching footswitch 107 and the endoscope mode switching footswitch 105. Similarly, in order to acquire a surgical energy device activation footswitch image (electric energy switching image) that is an image including the surgical energy device activation footswitch 108, a surgical energy device activation footswitch camera 112 (electric energy switching imaging unit) is disposed above the surgical energy device activation footswitch 108. In addition, the operation imaging unit is configured to include the master observation camera 40 and the surgical energy device activation footswitch camera 112.

The master arms 11A and 11B, the slave changeover switch 106, and the endoscope mode switching footswitch 105 are disposed on the top board 116 of the operation desk 115. The mode switching footswitch camera 111 and surgical energy device activation footswitch camera 112 are attached to a bottom part of the top board 116. The master observation camera 40 is attached to a support (not shown) of the operation desk 115.

The endoscope 45 may include an endoscope that is properly selected from endoscopes having a known configuration with a long insertion unit 46 shown in FIG. 1. An illumination unit or an imaging unit (not shown) is disposed at the distal end of the insertion unit 46. It is possible to acquire the internal-body image that is an image of the interior of the body of the patient P by inserting the insertion unit 46 into the body of the patient P. In this case, the endoscope 45 is mounted on the slave arm 21D.

As shown in FIG. 2, the master observation camera 40, the endoscope 45, the slave arm overhead camera 50, the mode switching footswitch camera 111, and the surgical energy device activation footswitch camera 112 are connected to the image processing circuit 60, and transmit the respective acquired images to the image processing circuit 60.

The image processing circuit 60 may include an image processing circuit having a known configuration. The image processing circuit 60 creates a synthetic image based on the setting operation mode set by the mode control circuit 55, converts information on the created synthetic image to a signal and transmits the signal to the display 65. The synthetic image is created such that the images transmitted from the master observation camera 40 and the like are arranged or overlapped.

In addition, in the image displayed on the display surface 66, although the positions of the endoscope 45 and the treatment tool of the slave arms 21A to 21D and the position of the treatment tool of the internal-body image are properly corrected in the drawings, this is intended to simplify the description.

Next, details of each mode of the mode control circuit 55 will be described. First, each mode within the ready mode M10 will be described. An operation image G11 is displayed on the display surface 66 in any of the standby mode M11, the standby surgical device exchange mode M12, the arm positioning mode M13, and the emergency stop mode M14 within the ready mode M10.

Figure 6:
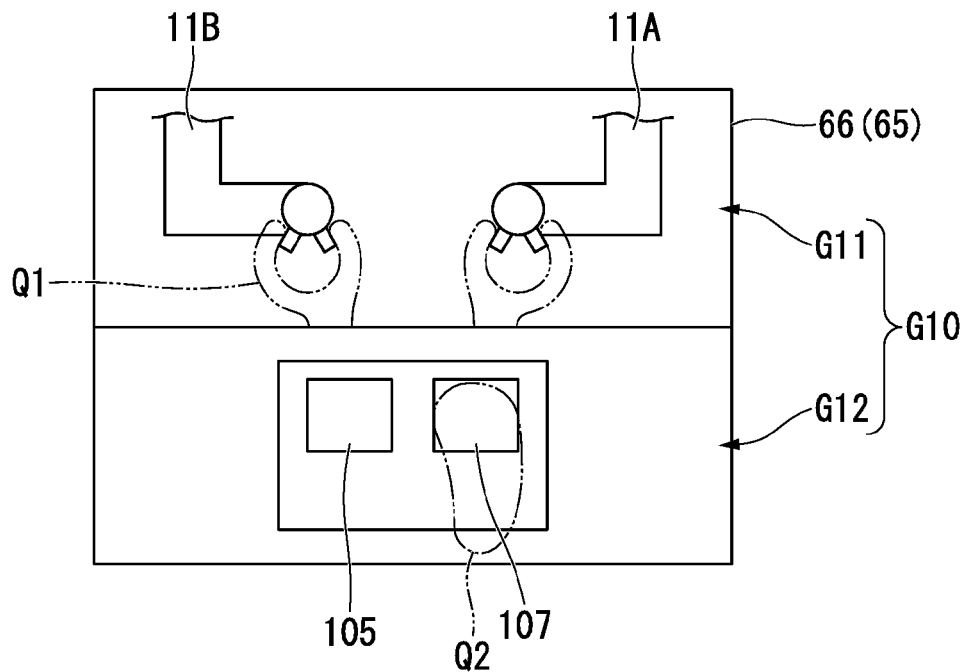
FIG. 6 is a diagram illustrating a synthetic image displayed on a display in a standby mode of the surgical assistant system in accordance with the embodiment of the present invention.

When the setting operation mode of the mode control circuit 55 is the standby mode M11, the slave arms 21A to 21D are in a standby state before the slave arms are capable of being operated by the operation of the operation unit. In particular, the slave control circuit 35 sets the arrangement angles $\theta A$ to $\theta C$ formed by the joint units 24A to 24C to the desired angles to fix the slave arms 21A to 21C based on the setting operation mode. Further, as shown in FIG. 6, the image processing circuit 60 creates a synthetic image G10 in which the operation image G11 including the master arms 11A and 11B acquired by the master observation camera 40 and a mode switching footswitch image G12 that is an image including the mode switching footswitch 107 and the endoscope mode switching footswitch 105 are arranged side by side based on the setting operation mode. The image processing circuit 60 converts the synthetic image G10 to a signal and transmits the signal. The transmitted signal is converted by a circuit (not shown) within the display 65, and the synthetic image G10 is displayed on the display surface 66.

When the surgeon grasps the master arms 11A and 11B with his or her hands, the hands Q1 are displayed in the operation image G11. In addition, when the surgeon steps on the mode switching footswitch 107 or the endoscope mode switching footswitch 105 with his or her foot, the foot Q2 is displayed in the mode switching footswitch image G12.

Figure 7:
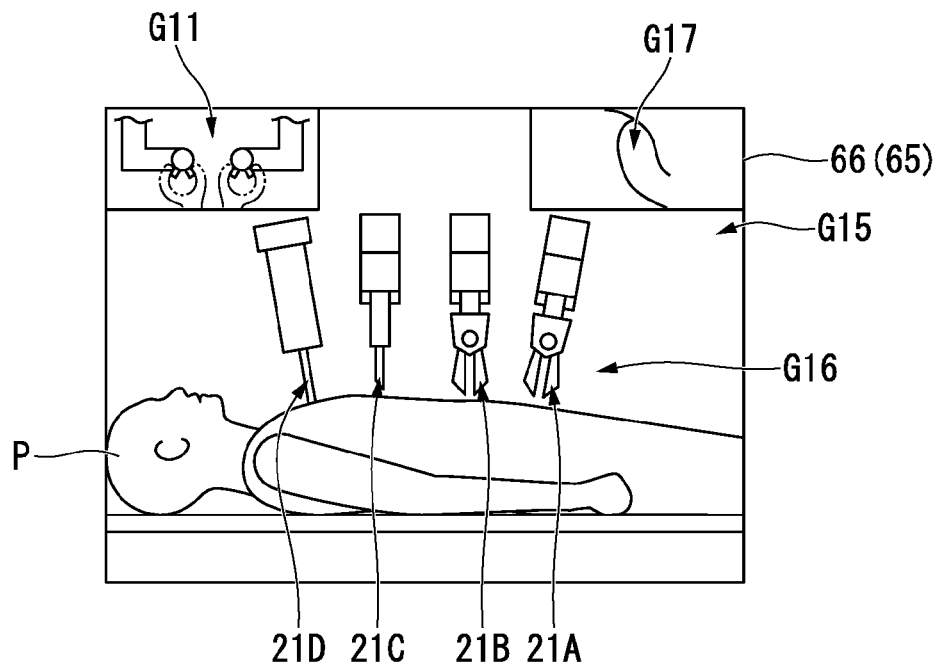
FIG. 7 is a diagram illustrating a synthetic image displayed on a display in a standby surgical device exchange mode of the surgical assistant system in accordance with the embodiment of the present invention.

When the setting operation mode is the standby surgical device exchange mode M12, the slave control circuit 35 sets the arrangement angles $\theta A$ to $\theta C$ formed by the joint units 24A to 24C to desired angles and fixes the slave arms 21A to 21C. Further, as shown in FIG. 7, the image processing circuit 60 creates a synthetic image G15 in which the operation image G11 and an internal-body image G17 acquired by the endoscope 45 are disposed at an edge of an arm image G16 including the slave arms 21A to 21D acquired by the slave arm overhead camera 50. The created synthetic image G15 is displayed on the display surface 66. In addition, only the distal end sides of the slave arms 21A to 21D are schematically illustrated in FIGS. 7, 8, 9, and 12.

Figure 8:
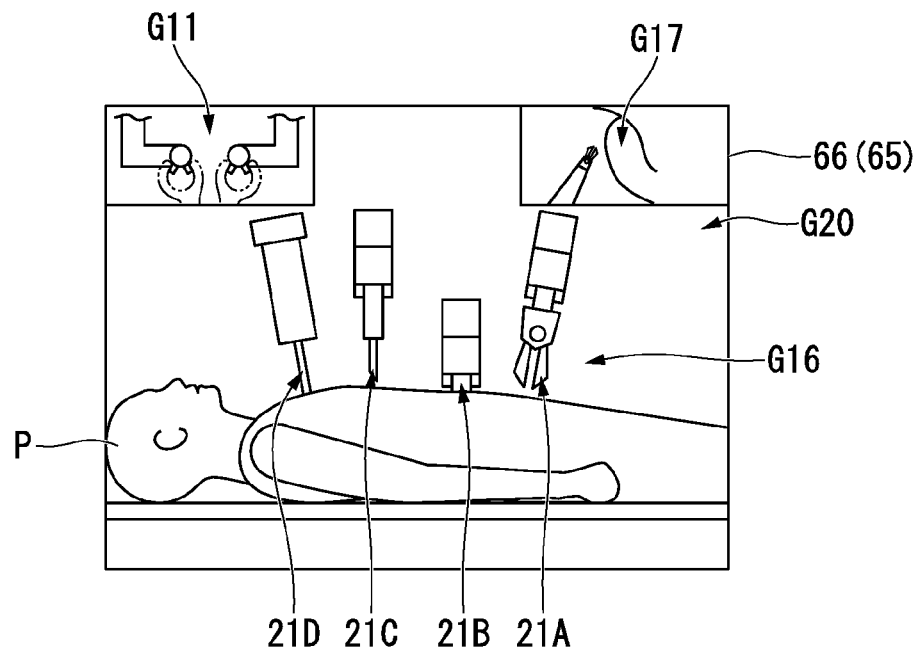
FIG. 8 is a diagram illustrating a synthetic image displayed on a display in an arm positioning mode of the surgical assistant system in accordance with the embodiment of the present invention.

When the setting operation mode is the arm positioning mode M13, the slave control circuit 35 causes an exert force to the joint units 24A to 24C so as to support the proximal end side support shafts 22A to 22C against gravity. Therefore, as the helper or the like directly and manually moves to the slave arms 21A to 21C, the positions of the leading end side support shafts 23A to 23C are capable of being adjusted. That is, holding force weaker than that for maintaining the arrangement angles $\theta A$ to $\theta C$ is exerted by the joint units 24A to 24C. Further, as shown in FIG. 8, the image processing circuit 60 creates a synthetic image G20 in which the operation image G11 and the internal-body image G17 are disposed at an edge of the arm image G16. The created synthetic image G20 is displayed on the display surface 66.

When the setting operation mode is the emergency stop mode M14, the slave control circuit 35 performs control such that a movement of the slave arms 21A to 21D to be forcibly stopped. In particular, supplying the electric energy to the joint unit 24A and transmitting the control signal are stopped.

Figure 9:
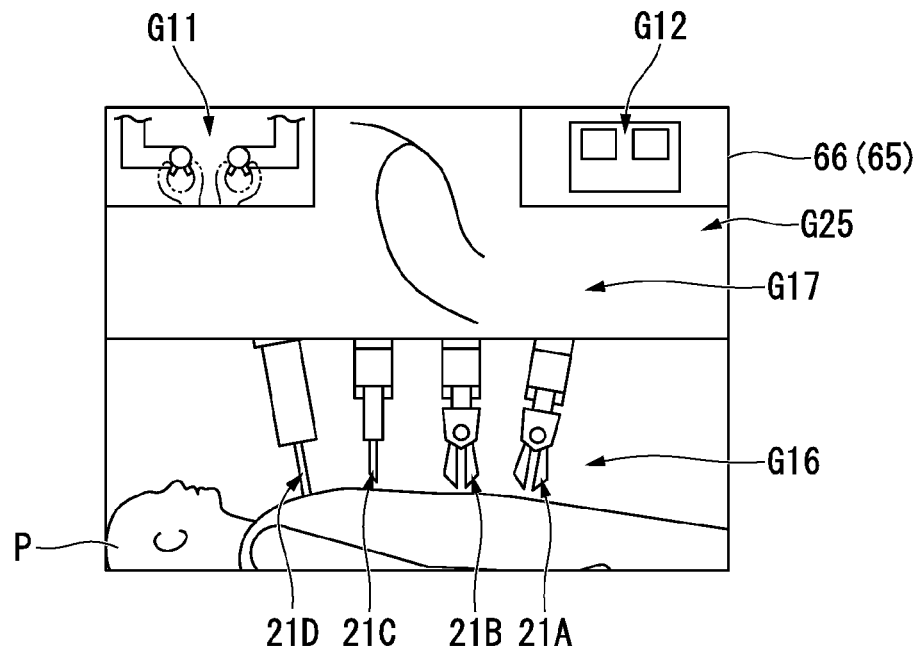
FIG. 9 is a diagram illustrating a synthetic image displayed on a display in an emergency stop mode of the surgical assistant system in accordance with the embodiment of the present invention.

Further, as shown in FIG. 9, the image processing circuit 60 creates a synthetic image G25 in which the operation image G11 and the mode switching footswitch image G12 are disposed at an edge of the image in which the internal-body image G17 and the arm image G16 are disposed side by side. The created synthetic image G25 is displayed on the display surface 66.

Next, each mode within the driving mode M20 will be described. The slave control circuit 35 causes the selected slave arm among the slave arms 21A to 21D to be operated based on the input given to the master arms 11A and 11B in any of the normal surgical device mode M21, the surgical energy device mode M22, the driving surgical device exchange mode M23, and the endoscope mode M24 within the driving mode M20. The internal-body image is displayed on the display surface 66.

Figure 10:
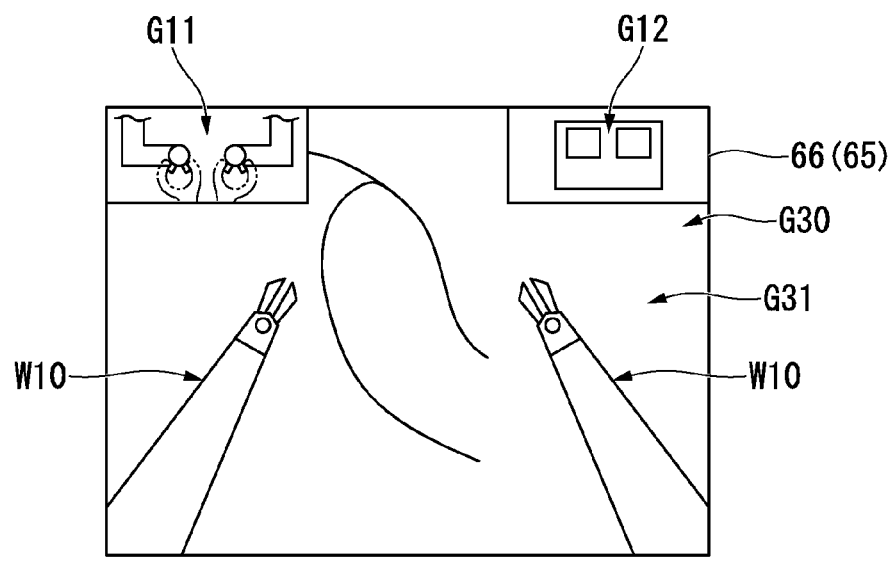
FIG. 10 is a diagram illustrating a synthetic image displayed on a display in a normal surgical device mode of the surgical assistant system in accordance with the embodiment of the present invention.

When the setting operation mode is the normal surgical device mode M21, as shown in FIG. 10, the image processing circuit 60 creates a synthetic image G30 in which the operation image G11 and the mode switching footswitch image G12 are disposed at an edge of an internal-body image G31. The created synthetic image G30 is displayed on the display surface 66.

Figure 11:
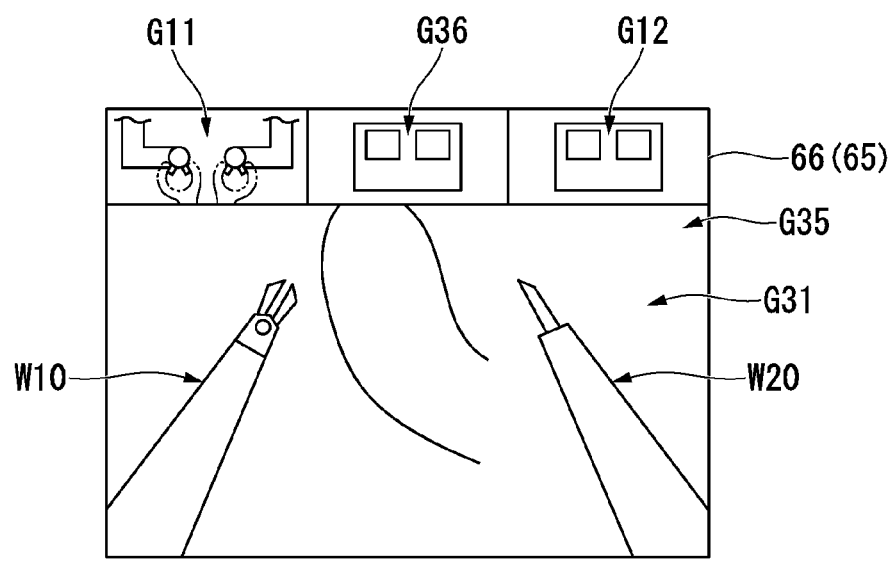
FIG. 11 is a diagram illustrating a synthetic image displayed on a display in a surgical energy device mode of the surgical assistant system in accordance with the embodiment of the present invention.

When the setting operation mode is the surgical energy device mode M22, as shown in FIG. 11, the image processing circuit 60 creates a synthetic image G35 in which the operation image G11, the mode switching footswitch image G12, and an surgical energy device activation footswitch image G36 acquired by the surgical energy device activation footswitch camera 112 are disposed at an edge of the internal-body image G31. The created synthetic image G35 is displayed on the display surface 66.

Figure 12:
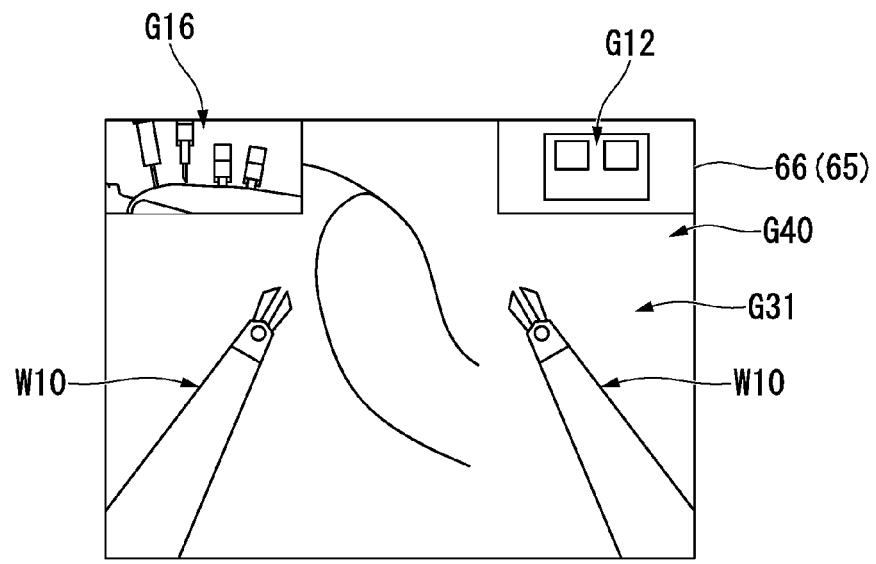
FIG. 12 is a diagram illustrating a synthetic image displayed on a display in a driving surgical device exchange mode of the surgical assistant system in accordance with the embodiment of the present invention.

When the setting operation mode is the driving surgical device exchange mode M23, as shown in FIG. 12, the image processing circuit 60 creates a synthetic image G40 in which the arm image G16 and the mode switching footswitch image G12 are disposed at an edge of the internal-body image G31. The created synthetic image G40 is displayed on the display surface 66.

Figure 13:
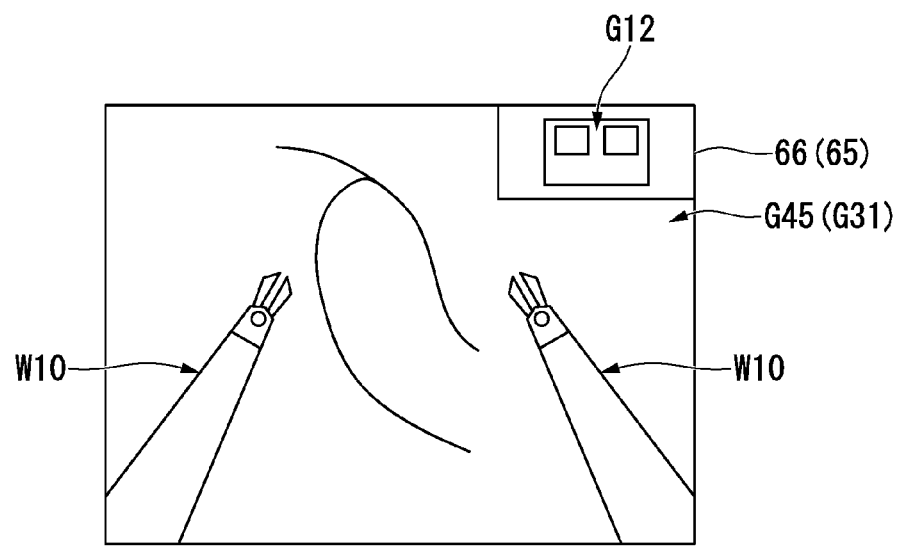
FIG. 13 is a diagram illustrating a synthetic image displayed on a display in an endoscope mode of the surgical assistant system in accordance with the embodiment of the present invention.

When the setting operation mode is the endoscope mode M24, as shown in FIG. 13, the image processing circuit 60 creates a synthetic image G45 in which the mode switching footswitch image G12 is disposed at an edge of the internal-body image G31. The created synthetic image G45 is displayed on the display surface 66.

In addition, when the surgical assistant system 1 is started up, the setting operation mode is set to the standby mode M11.

Next, operations of the surgical assistant system 1 configured as described above will be described.

Since the setting operation mode is in the standby mode M11 when the surgical assistant system 1 is started up, the slave arms 21A to 21C are fixed by the slave control circuit 35. The synthetic image G10 created by the image processing circuit 60 and shown in FIG. 6 is displayed on the display surface 66 of the display 65.

A helper A lays the patient P on the surgical table 101, and performs appropriate treatment such as sterilization or anesthesia.

A surgeon Q sits on a chair (not shown) disposed in front of the operation desk 115 and grasps the master arms 11A and 11B with his or her right and left hands, respectively. His or her face is toward the display surface 66.

Since the operation image G11 and the mode switching footswitch image G12 are displayed on the display surface 66, it is possible for the surgeon Q to confirm the state in which the master arms 11A and 11B, the endoscope mode switching footswitch 105, and the mode switching footswitch 107 are being operated on the display surface 66 even while the surgeon is carefully watching the display surface 66.

When the helper A presses the surgical device exchange switch 36 to change the setting operation mode from the standby mode M11 to the standby surgical device exchange mode M12, the synthetic image G15 including the image of the slave arms 21A to 21D shown in FIG. 7 is displayed on the display surface 66. For example, the helper A mounts the grasping forceps W10 on each of the holding units 26A to 26C of the slave arms 21A to 21C in response to contents of the procedure in accordance with the instruction of the surgeon Q. The surgeon Q confirms that the treatment tools are mounted on the slave arms 21A to 21C by virtue of the display surface 66. In this case, the identification unit 102 confirms the kind of the treatment tool attached to the slave arm 21C.

When the treatment tool is mounted to finish the treatment tool exchange, the setting operation mode is switched to the standby mode M11. For example, it is preferable that the switching be automatically performed when it is detected that the treatment tool is mounted by having a detection unit that detects that the treatment tool is mounted on the treatment tool device. However, the switching may be performed by disposing a switch such as the surgical device exchange switch 36 to be switched to the standby mode M11 within the viewing range 41 and pressing the switch.

When the helper A presses the positioning switch 37 to switch the setting operation mode to the arm positioning mode M13, the synthetic image G20 including the slave arms 21A to 21D shown in FIG. 8 is displayed on the display surface 66.

The helper A moves the distal end side support shaft 23A of the slave arm 21A with his or her own power, and introduces the treatment tool from the Trocar (not shown) inserted into the patient P or the insertion unit 46 of the endoscope 45 into the body. Since the image of the helper A moving the distal end side support shaft 23A is displayed on the display surface 66, the surgeon Q confirms that positioning of the slave arm 21A is being properly performed.

When the positioning of the arm is finished, the setting operation mode is switched to the standby mode M11. For example, it is preferable that the switching be automatically performed when the switch disposed in the slave arms 21A to 21D is pressed to perform the positioning and the switch is taken off after the positioning. However, a switch such as the positioning switch 37 to be switched to the standby mode M11 may be disposed within the viewing range 41 and the switch may be pressed to perform the switching as described above.

When some kind of urgent problem occurs with the surgical assistant system 1, the surgeon Q or the helper A presses the emergency stop switch 38 to switch to the emergency stop mode M14. This enables the electric energy supplied to the joint units 24A to 24D to be stopped. Further, the synthetic image G25 including the internal-body image G17 and the arm image G16 shown in FIG. 9 is displayed on the display surface 66.

When it is time to actually administer treatment to the patient P using the treatment tool, the surgeon Q presses the mode switching footswitch 107 with his or her foot Q2. When the mode control circuit 55 does not receive the signal indicating that the surgical energy device is mounted on the slave arms 21A to 21C, the mode control circuit switches the setting operation mode to the normal surgical device mode M21. The synthetic image G30 in which the operation image G11 and the mode switching footswitch image G12 are disposed at an edge of the internal-body image G31 shown in FIG. 10 is then displayed on the display surface 66. The internal-body image G31 is an image acquired by an imaging unit of the endoscope 45.

The slave changeover switch 106 is operated to select the slave arms 21A and 21B that will follow the master arms 11A and 11B among the slave arms 21A to 21D. By operating the master arms 11A and 11B, proper treatment is performed on the patient P using the grasping forceps W10. Meanwhile, the slave arms 21C and 21D are stopped.

Since the synthetic image G30 including the internal-body image G31 is displayed on the display surface 66, it is possible for the surgeon Q to perform the treatment while confirming the state of the interior of the body of the patient P by virtue of the synthetic image 30.

When the surgeon Q determines to perform the treatment using the high-frequency electric knife W20, the surgeon instructs the helper A to press the surgical device exchange switch 36 and switch the setting operation mode from the normal surgical device mode M21 to the driving surgical device exchange mode M23. The synthetic image G40 in which the arm image G16 and the mode switching footswitch image G12 are disposed at an edge of the internal-body image G31 shown in FIG. 12 is then displayed on the display surface 66.

The helper A removes the grasping forceps W10 from the slave arm 21C that is currently stopped, and mounts the high-frequency electric knife W20 on the holding unit 26C of the slave arm 21C. The surgeon Q confirms that the proper treatment tool is mounted on the slave arm 21C by virtue of the image of the slave arm 21C displayed on the display surface 66.

When the identification unit 102 detects that the high-frequency electric knife W20 is mounted on the slave arm 21C, the slave changeover switch 106 may be operated to switch the setting operation mode to the surgical energy device mode M22. In particular, when it is detected that the high-frequency electric knife W20 is mounted on the slave arm that may be operated by following the master arms 11A and 11B, the slave changeover switch 106 may be operated to switch the setting operation mode to the surgical energy device mode M22.

The surgeon Q operates the slave changeover switch 106 to switch the slave arm capable of being operated by following the master arm 11B from the slave arm 21B to the slave arm 21C. In this case, since it is detected that the high-frequency electric knife 21C is mounted on the slave arm 21C, the setting operation mode is switched to the surgical energy device mode M22. The synthetic image G35 in which the operation image G11, the mode switching footswitch image G12, and the surgical energy device activation footswitch image G36 are disposed at an edge of the internal-body image G31 shown in FIG. 11 is then displayed on the display surface 66.

The surgeon Q operates the master arm 11B to dispose the high-frequency electric knife W20 near the patient P.

The surgeon operates the surgical energy device activation footswitch 108 to supply the high-frequency current to the high-frequency electric knife W20 mounted on the slave arm 21C and make an incision in the affected part while confirming the internal-body image G31 and the surgical energy device activation footswitch image G36 within the synthetic image G35 displayed on the display surface 66.

The surgeon Q operates the endoscope mode switching footswitch 105 when trying to operate the endoscope 45 mounted on the slave arm 21D. The setting operation mode is then switched to the endoscope mode M24. The synthetic image G45 in which the mode switching footswitch image G12 is disposed at an edge of the internal-body image G31 shown in FIG. 13 is displayed on the display surface 66.

In this way, the surgeon Q administers treatment to the patient P by operating the master arms 11A and 11B, the slave changeover switch 106, the mode switching footswitch 107, and the surgical energy device activation footswitch 108 while always watching the display surface 66 and giving an instruction to the helper A.

As described above, in the surgical assistant system 1 according to the present embodiment, the operation image G11 is displayed on the display 65 in any mode within the ready mode M10. Therefore, even when the surgeon Q is carefully watching the display 65, it is possible to recognize the positions of the master arms 11A and 11B by virtue of the operation image G11 displayed on the display 65. The surgeon Q can thus suppress the time taken to find the master arms 11A and 11B.

In the standby mode M11, since the operation image G11 and the mode switching footswitch image G12 are displayed together, it is possible to suppress the time taken for the surgeon Q to find the master arms 11A and 11B, the endoscope mode switching footswitch 105, and the mode switching footswitch 107 while preventing the master arms 11A and 11B, the endoscope mode switching footswitch 105, and the mode switching footswitch 107 from being operated by mistake.

When the positioning switch 37 is operated to switch the setting operation mode to the arm positioning mode M13, it is possible for the surgeon Q to quickly respond to the emergency occurrence by confirming the arm image G16 displayed on the display 65.

By operating the surgical device exchange switch 36, the setting operation mode is switched to the standby surgical device exchange mode M12. By displaying the arm image G16 including the slave arms 21A to 21D on the display 65, it is possible for the surgeon Q carefully watching the display 65 to confirm the treatment tool to be attached to or detached from the slave arms 21A to 21D by the helper A. In addition, by confirming the arm image G16, it is possible for the surgeon Q to quickly respond to the emergency occurrence.

In the standby surgical device exchange mode M12, the image processing circuit 60 creates the synthetic image G15 in which the operation image G11 and the internal-body image G17 are disposed at an edge of the arm image G16. Therefore, even while the surgeon Q carefully watching the display 65 mainly observes the arm image G16, it is possible for the surgeon to confirm the state in which the surgeon is grasping the master arms 11A and 11B or the internal-body image G17 acquired by the endoscope 45.

By operating the emergency stop switch 38, the setting operation mode is switched to the emergency stop mode M14. In the emergency stop mode M14, the electric energy supplied to the joint units 24A to 24D is stopped. The synthetic image G25 including the internal-body image G17, the arm image G16, and the mode switching footswitch image G12 is displayed on the display surface 66. The surgeon Q can confirm the safety of the patient P and the surgical assistant system 1 by confirming the internal-body image of the patient P and the situation around the slave arms 21A to 21D and can also quickly respond to the emergency occurrence.

By operating the surgical device exchange switch 36, the setting operation mode is switched to the driving surgical device exchange mode M23. Since not only the internal-body image G31 but also the arm image G16 including the slave arms 21A to 21D is displayed on the display 65, the surgeon Q carefully watching the display 65 can confirm the treatment tool (treatment tool attached to or detached from the slave arms 21A to 21D by the helper A).

In the driving surgical device exchange mode M23, the synthetic image G40 in which the arm image G16 and the mode switching footswitch image G12 are disposed at an edge of the internal-body image G31 is displayed on the display 65. The surgeon Q can confirm the treatment tool that is attached to or detached from the slave arms 21A to 21C by virtue of the arm image G16 even while mainly observing the internal-body image G31 and operating the master arms 11A and 11B to administer treatment.

By operating the mode switching footswitch 107 when the high-frequency electric knife W20 is mounted on the holding units 26A to 26C, the setting operation mode is switched to the surgical energy device mode M22.

In the surgical energy device mode M22, since the surgical energy device activation footswitch image G36 is displayed at an edge of the internal-body image G31, the surgeon Q can confirm the surgical energy device activation footswitch image G36 even while mainly observing the internal-body image G31. Further, the mode switching footswitch image G12 and the surgical energy device activation footswitch image G36 are displayed on the display 65. Therefore, it is possible to prevent the surgeon Q from hesitating to select the desired switch among a plurality of the footswitches 107 and 108 or operating the footswitches 107 and 108 by mistake.

The embodiment of the present invention has been described with reference to drawings. However, the particular configuration is not limited to the embodiment, and changes in configuration not departing from the scope of the present invention are also included. For example, in the present embodiment, the number of master arms and slave arms may be properly set in response to the specification of the surgical assistant system. The operation unit is the master arms 11A and 11B. However, the operation unit may be an operation unit having a different configuration such as a so-called joystick.

In the present embodiment, the image processing circuit 60 creates the synthetic image G15 in which the operation image G11 and the internal-body image G17 are disposed at an edge of the arm image G16 in the standby surgical device exchange mode M12. However, the synthetic image created in the standby surgical device exchange mode M12 is not limited thereto. For example, the synthetic image may be one in which only the operation image G11 is disposed at the edge of the arm image G16. The synthetic image may be configured such that the arm image G16, the operation image G11, and the internal-body image G17 having the same size as each other are arranged.

In the present embodiment, the image processing circuit 60 creates the synthetic image G30 in which the operation image G11 and the mode switching footswitch image G12 are disposed at the edge of the internal-body image G31 in the normal surgical device mode M21. However, the image processing circuit 60 may create and display the synthetic image using only the internal-body image 31.

In the present embodiment, the image processing circuit 60 creates the synthetic image G40 in which the arm image G16 and the mode switching footswitch image G12 are disposed at the edge of the internal-body image G31 in the driving surgical device exchange mode M23. However, the synthetic image in which the internal-body image G31 and the arm image 16 are arranged may be created.

In addition, the operation image G11 may be set to be displayed on the display surface 66 in each mode within the driving mode M20 as well as the ready mode M10.

The surgical energy device activation footswitch image G36 may also be set to be displayed even in the driving surgical device exchange mode M23 or the endoscope mode M24.

In the present embodiment, the first and second identification units are configured to have electric resistors of which the resistance values are different from each other and to enable an identification unit to detect the resistance values of the electric resistors. However, the first identification, the second identification, and the identification unit are not limited thereto, and various configurations that will be described below may be employed.

For example, the connection state regarding whether or not the electric resistor having a constant resistance value is connected between treatment tool side electrodes of each pair with respect to the entire N pairs of the treatment tool side electrodes is changed for each kind of the treatment tool while the N pairs of the treatment tool side electrodes are exposed and disposed in the treatment tool. The identification unit identifies ON when the treatment tool side electrodes of each pair are connected via the electric resistor and identifies OFF when the treatment tool side electrodes of each pair are not connected via the electric resistor. The kind of the treatment tool is identified in the manner of binary system by combining the N ONs or OFFs.

N positions in which convex portions are disposed on the outer surface of the treatment tool are arranged. All of the N positions are combined in association with whether or not the convex portions are disposed in each of the setting positions, that is, the outer shape of the treatment tool is changed for each kind of the treatment tool. The kind of the treatment tool is identified by causing the N switches disposed in the identification unit side to detect whether or not the convex portions are disposed in the respective setting positions.

In addition, as a different configuration of the identification unit, identification information such as a bar code is disposed in the treatment tool and information included in the identification information is changed for each kind of the treatment tool. The kind of the treatment tool is identified by the identification unit detecting and reading the identification information.

In the present embodiment, the setting operation mode is configured to be arbitrarily switched among the standby mode M11, the standby surgical device exchange mode M12, the arm positioning mode M13, and the emergency stop mode M14, and among the normal surgical device mode M21, the surgical energy device mode M22, the driving surgical device exchange mode M23, and the endoscope mode M24 except between the standby surgical device exchange mode M12 and the arm positioning mode M13. However, the setting operation mode may be switched only between the standby mode M11 and the standby surgical device exchange mode M12, between the standby mode M11 and the arm positioning mode M13, and between the standby mode M11 and the emergency stop mode M14 within the ready mode M10. This also applies to the driving mode M20 in the same way.

In the ready mode M10 and the driving mode M20, all of the modes mentioned above are not limited to some cases, and a proper mode is properly set by the device configuration. For example, when it is difficult to exchange the treatment tool in the slave arms 21A to 21C (e.g., an integrated structure of the slave arm and the treatment tool), the treatment tool exchange mode may be omitted in the ready mode M10 and the driving mode M20. In addition, when the surgical energy device is not used, the surgical energy device mode M22 may be omitted in the driving mode M20. When the standby mode M11 is included in the ready mode M10, the other modes may be properly set. The modes other than the normal surgical device mode M21 may be properly set even in the driving mode M20.

In addition, the configuration of the operation unit is not limited to the master arm, and may employ the joystick. In addition, when the surgical energy device is not used in the configuration of the surgical assistant system as described above, the surgical energy device activation footswitch or the like may be omitted. The configuration of the operation unit is properly set by the configuration of the surgical assistant system, the number of the modes to be set, and so forth. In a similar way, the operation imaging unit is properly set by the configuration of the surgical assistant system, the number of the modes to be set, and so forth.

The nonelectric type surgical device may include the treatment tool such as a needle holder or scissors that is properly selected in addition to the grasping forceps W10. On the other hand, the electric type surgical device may include an ultrasonic surgical device or a snare in addition to the high-frequency electric knife W20.

In the present embodiment, the surgical device exchange switch 36, the positioning switch 37, and the emergency stop switch 38 are disposed in the base of the slave arm as shown in FIG. 4. However, these switches 36, 37, and 38 may be disposed in positions within the viewing range 41 of the master observation camera 40. In addition, these switches 36, 37, and 38 may be disposed in both of the base and positions within the viewing range 41.

In the present embodiment, the slave arms are switched by operating the slave changeover switch 106. However, the slave arms may be switched by operating the mode switching footswitch 107. For example, when the mode switching footswitch 107 is pressed for a short time in the ready mode M10, the slave arms 21A and 21B are allocated to the respective master arms 11A and 11B, and are transitioned to the driving mode M20 and can thus be operated. Next, when the mode switching footswitch 107 is pressed for a short time, the slave arm 21C is allocated to the master arm 11A, the slave arm 21A is stopped for the occasion, and the slave arm 21C is thus capable of being operated. Which slave arms 21A to 21D are allocated to the master arms 11A and 11B is set beforehand. When the mode is transitioned from the driving mode M20 to the ready mode M10, the mode switching footswitch 107 is pressed for a long time. In this case, since a timer is built in the mode control circuit 55 and the time taken for which the signal is continuously transmitted from the mode switching footswitch 107 is measured, it is recognized, namely, that the mode switching footswitch 107 is pressed for a long time or a short time.

While preferred embodiments of the present invention have been described and illustrated above, it should be understood that these are exemplary of the present invention and are not to be considered as limiting. Additions, omissions, substitutions, and other modifications can be made without departing from the spirit or scope of the present invention. Accordingly, the present invention is not to be considered as being limited by the foregoing description, and is only limited by the scope of the appended claims.

What is claimed is:

1. A surgical assistant system comprising:
    an operation unit configured to give an input;
    an arm unit on which a treatment tool is mounted;
    an operation imaging unit configured to acquire an operation image that is an image including the operation unit;
    an endoscope configured to acquire an internal-body image including an image of an interior of a body of a patient;
    a mode control unit having a plurality of operation modes and configured to enable one of the plurality of operation modes to be set as a setting operation mode;
    a driving unit configured to enable the arm unit to be operated based on the input given by the operation unit and the setting operation mode;
    a synthetic image creation unit configured to synthesize images using at least the operation image to create a synthetic image based on the setting operation mode; and
    a display unit configured to display the synthetic image.

2. The surgical assistant system according to claim 1, further comprising:
    a mode switching unit configured to switch the operation modes,
    wherein the operation modes include:
    a ready mode in which the arm unit is in a state before being operatable by the operation unit and the synthetic image creation unit creates the synthetic image including the operation image; and
    a driving mode in which the driving unit is capable of operating the arm unit based on the input given by the operation unit and the synthetic image creation unit creates the synthetic image including the operation image and the internal-body image, and
    the mode switching unit switches the operation mode set as the setting operation mode between the ready mode and the driving mode by transmitting a signal to the mode control unit.

3. The surgical assistant system according to claim 2, further comprising:
    an arm imaging unit configured to acquire an arm image that is an image including the arm unit,
    wherein the synthetic image creation unit creates the synthetic image by synthesizing images using the arm image.

4. The surgical assistant system according to claim 3, further comprising:
    a positioning switching unit configured to switch the operation modes,
    wherein the ready mode includes:
    a standby mode in which the arm unit is in a standby state in which the arm unit waits in a state before being operatable by the operation unit and the synthetic image creation unit creates the synthetic image including the operation image; and
    a positioning mode in which a position of the arm unit is capable of being adjusted and the synthetic image creation unit creates the synthetic image including the operation image and the arm image, and
    the positioning switching unit switches the operation mode set as the setting operation mode between the standby mode and the positioning mode by transmitting a signal to the mode control unit.

5. The surgical assistant system according to claim 3, further comprising:
    a standby exchange switching unit configured to switch the operation modes,
    wherein the arm unit enables the treatment tool to be detachable,
    the ready mode includes:
    a standby mode in which the arm unit is in a standby state in which the arm unit waits in a state before being operatable by the operation unit and the synthetic image creation unit creates the synthetic image including the operation image; and a standby surgical device exchange mode in which the arm unit is in a state before being capable of being operated by the operation unit and the synthetic image creation unit creates the synthetic image including the operation image, the internal-body image, and the arm image in a state in which the treatment tool is exchangeable, and the standby exchange switching unit switches the operation mode set as the setting operation mode between the standby mode and the standby surgical device exchange mode by transmitting a signal to the mode control unit.

6. The surgical assistant system according to claim 5, wherein the synthetic image creation unit creates the synthetic image in which the operation image and the internal-body image are disposed at an edge of the arm image in the standby surgical device exchange mode.

7. The surgical assistant system according to claim 3, further comprising:

an emergency stop switching unit configured to switch the operation modes, wherein the ready mode includes:

a standby mode in which the arm unit is in a standby state in which the arm unit waits in a state before being operatable by the operation unit and the synthetic image creation unit creates the synthetic image including the operation image; and an emergency stop mode in which an operation of the arm unit is forcibly stopped and the synthetic image creation unit creates the synthetic image including the operation image, the internal-body image, and the arm image, and the emergency stop switching unit switches the operation mode set as the setting operation mode between the standby mode and the emergency stop mode by transmitting a signal to the mode control unit.

8. The surgical assistant system according to claim 3, further comprising:

a driving exchange switching unit configured to switch the operation modes, wherein the arm unit enables the treatment tool to be detachable, the driving mode includes:

a driving normal surgical device mode in which the synthetic image creation unit creates the synthetic image using the operation image and the internal-body image in a state in which the arm unit is operated by the operation unit; and a driving surgical device exchange mode in which the treatment tool is exchangeable and the synthetic image creation unit creates the synthetic image including the operation image, the internal-body image, and the arm image in the state in which the arm unit is operated by the operation unit, and the driving exchange switching unit switches the operation mode set as the setting operation mode between the driving normal surgical device mode and the driving surgical device exchange mode by transmitting a signal to the mode control unit.

9. The surgical assistant system according to claim 8, wherein the synthetic image creation unit creates the synthetic image in which the operation image and the arm image are disposed at an edge of the internal-body image in the driving surgical device exchange mode.

10. The surgical assistant system according to claim 3, further comprising:

an electric energy switching imaging unit configured to be a part of the operation imaging unit; and a driving electric mode switching unit configured to switch the operation modes, wherein the treatment tool is divided into a nonelectric type surgical device that does not use electric energy and an electric type surgical device that uses electric energy, the operation unit has an electric energy switching unit switching whether or not electric energy is supplied to the electric type surgical device as a part of the operation unit, the electric energy switching imaging unit acquires an electric energy switching image that is an image including the electric energy switching unit, the operation image includes the electric energy switching image, the driving mode includes:

a driving normal surgical device mode in which the synthetic image creation unit creates the synthetic image using the operation image and the internal-body image in a state in which the arm unit is operated by the operation unit; and a driving electricity treatment tool mode in which the synthetic image creation unit creates the synthetic image including the internal-body image and the electric energy switching image, and the driving electric mode switching unit switches the operation mode set as the setting operation mode between the driving normal surgical device mode and the driving electricity treatment tool mode by transmitting a signal to the mode control unit.

11. The surgical assistant system according to claim 1, further comprising:

an arm imaging unit configured to acquire an arm image that is an image including the arm unit, wherein the synthetic image creation unit creates the synthetic image by synthesizing images using the arm image.

* * * * *